US005583278A

United States Patent [19]

Alt et al.

[11] Patent Number: 5,583,278
[45] Date of Patent: Dec. 10, 1996

[54] RECOMBINATION ACTIVATING GENE DEFICIENT MOUSE

[75] Inventors: Frederick W. Alt; Yoichi Shinkai, both of Boston, Mass.

[73] Assignee: The Trustees of Columbia University in the City of New York, New York, N.Y.

[21] Appl. No.: 248,638

[22] Filed: May 24, 1994

Related U.S. Application Data

[63] Continuation of Ser. No. 847,565, Mar. 5, 1992, abandoned.

[51] Int. Cl.⁶ .......................... C12N 15/00; A61K 49/00; A61K 39/00
[52] U.S. Cl. .................. 800/2; 800/DIG. 1; 800/DIG. 3; 435/172.3; 435/320.1; 424/9.2; 424/204.1; 424/234.1; 935/111
[58] Field of Search ................................ 800/2, DIG. 1, 800/DIG. 2, DIG. 3; 435/172.3, 317.1, 320.1; 424/9, 9.2, 204.1, 234.1; 935/62, 111

[56] References Cited

PUBLICATIONS

Koller et al., Science 248: 1227–1230 (1990).
Zimmer et al., Nature 338: 150–153 (1989).
Robertson, Biology of Reproduction 44: 238–245 (1991).
Andriole, Amer. J. Medicine 82(4A): 67–70 (1987).
Biederman, K. A., et al., *Proc. Natl. Acad. Sci., U.S.A.*, vol. 88, pp. 1394–1397 (1991).
Blackwell, T. K., et al., *J. Biol. Chem.*, vol. 264, pp. 10327–10330 (1989).
Bosma, M. J., et al., *Annu. Rev. Immunol.* vol. 9, pp. 323–350 (1990).
Carroll, A. M., et al., *Genes Dev.*, vol. 5, pp. 1357–1366 (1991).
Ferrier, P., et al., *J. Exp. Med.*, vol. 171, pp. 1900–1918 (1990).
Fulop, G. M., et al., *Nature*, vol. 347, pp. 479–482 (1990).
Hardy, R. R., et al., *Cur. Topics in Microbiol. & Immunol.*, vol. 152, pp. 19–251 (1989).
Lewis, S., et al., *Cell*, vol. 59, pp. 585–588 (1989).
Lieber, M. R., et al., *Genes Dev.*, vol. 1, pp. 751–761 (1987).
London, N. J. M., et al., *Transplant Proc.*, vol. 23, pp. 749 (1991).
McCune, J. M., *Curr. Opin. Immunol.*, vol. 3, pp. 224–228 (1991).
Oettinger, M. A., et al., *Science*, vol. 248, pp. 1517–1523 (1990).
Phillips, R. A., et al., *Curr. Top. Microbiol. Immunol.* vol. 152, pp. 259–263 (1989).
Turka, L. A., et al., *Science*, vol. 253, pp. 778–781 (1991).

*Primary Examiner*—Jasmine C. Chambers
*Attorney, Agent, or Firm*—John P. White

[57] ABSTRACT

This invention relates to a recombinant mouse with both alleles of recombination activating gene 2 being functionally deficient. This invention discloses the method to make such mouse and the uses of such mouse.

18 Claims, 10 Drawing Sheets

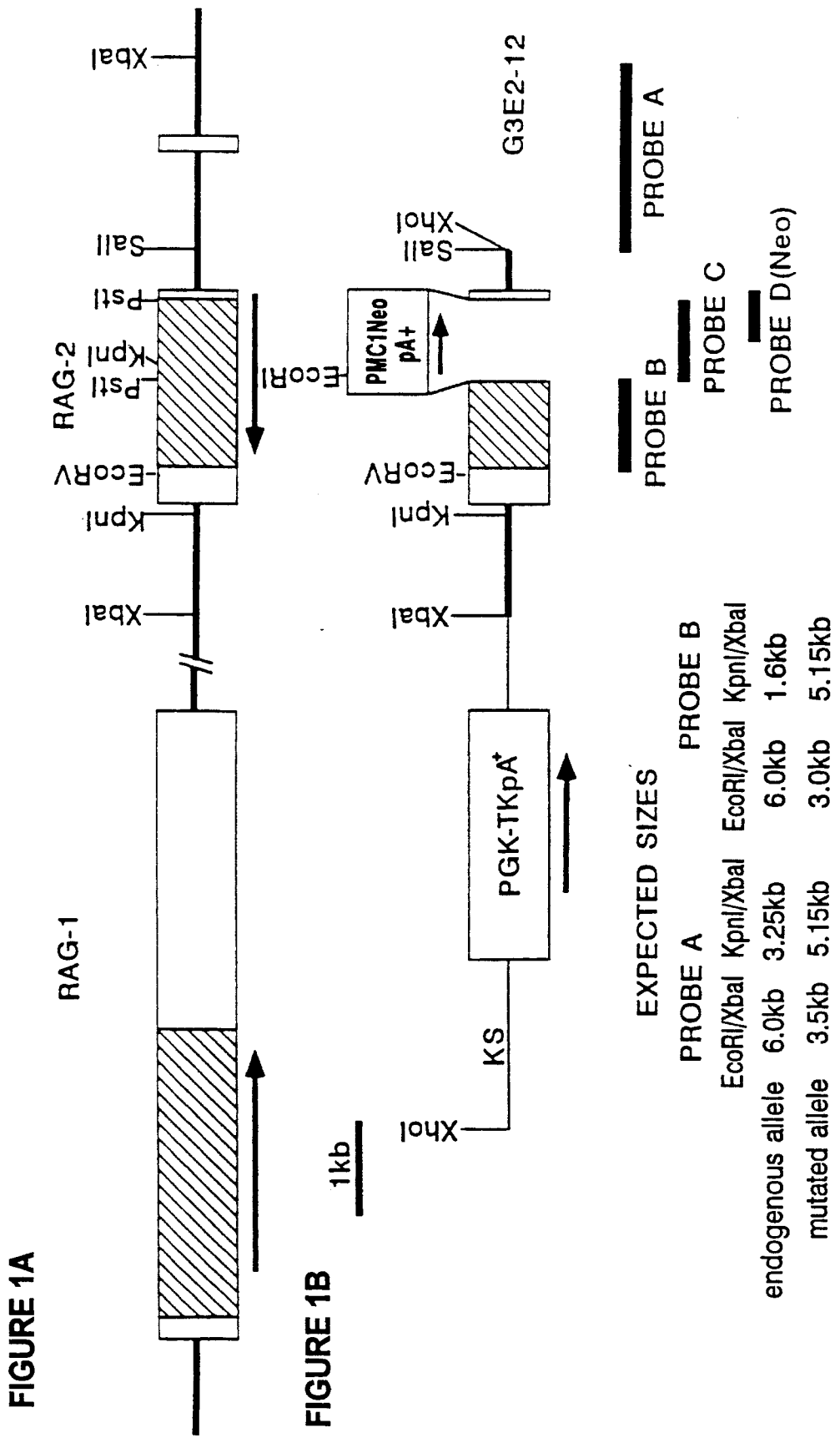

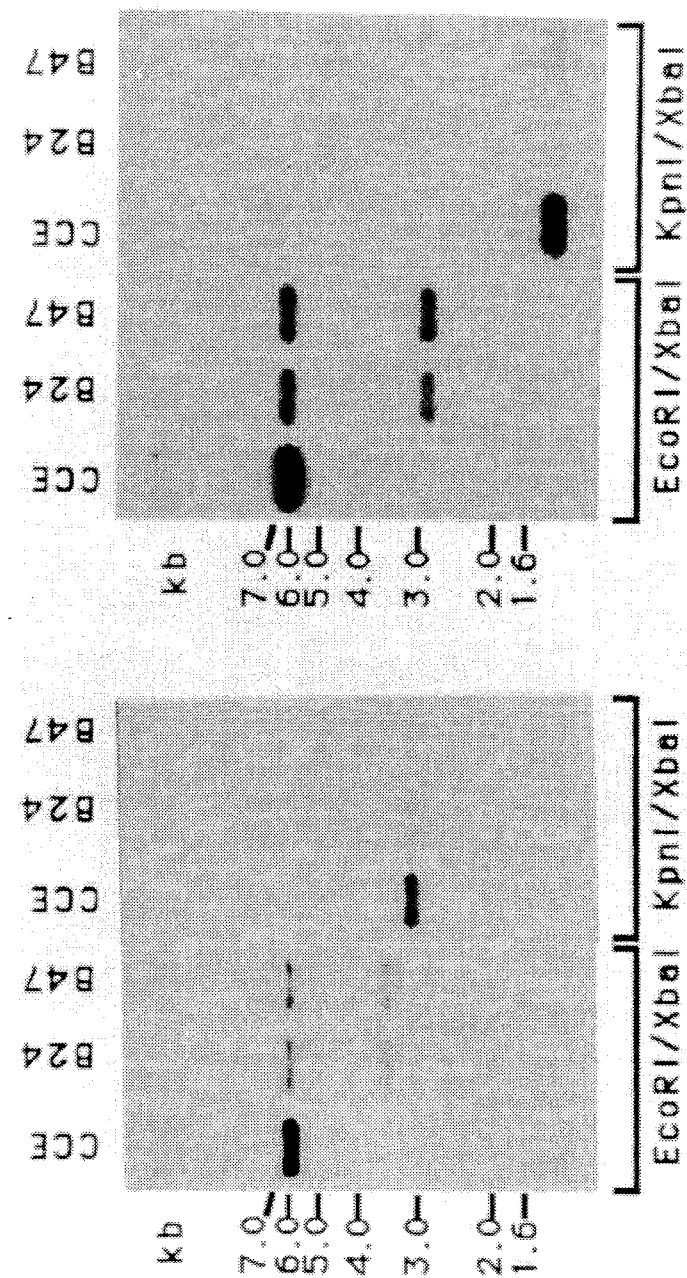

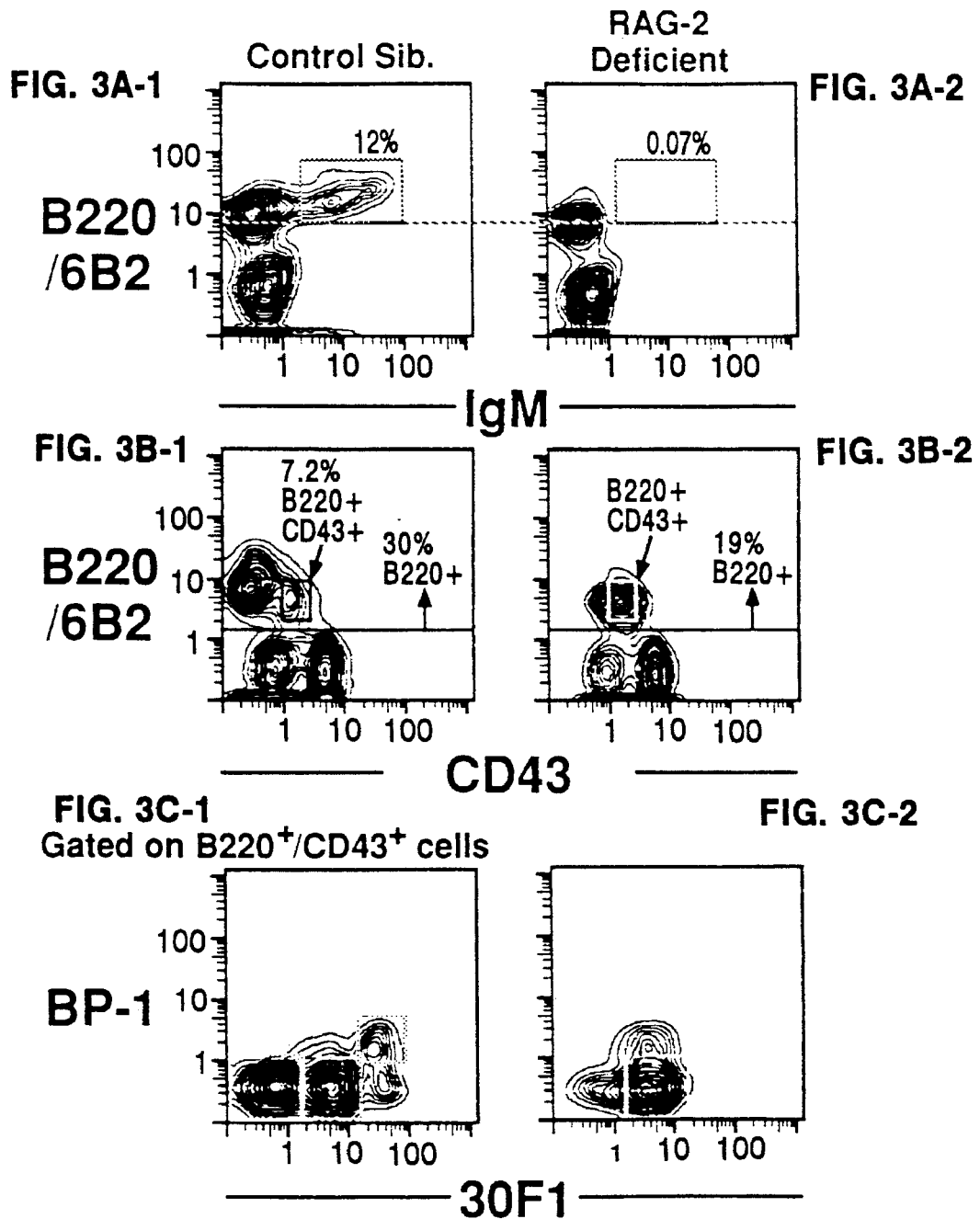

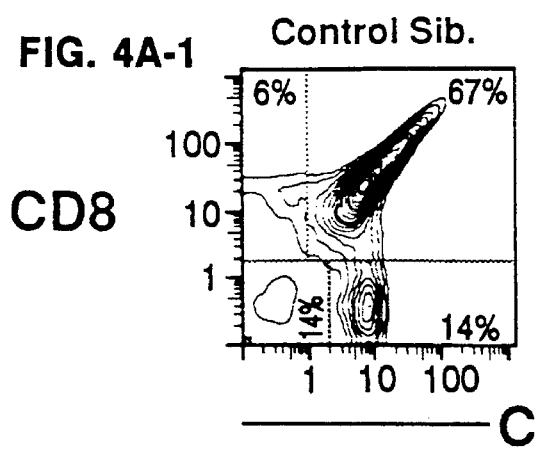
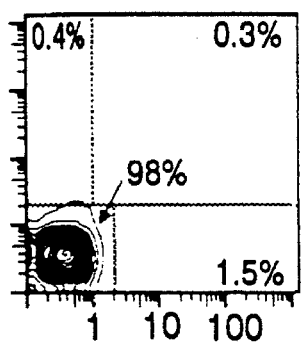
FIG. 4A-1  FIG. 4A-2
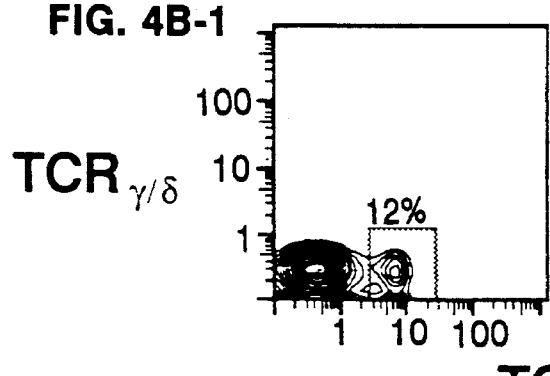
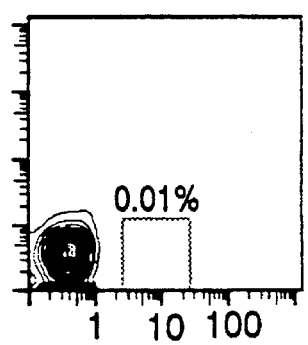
FIG. 4B-1  FIG. 4B-2
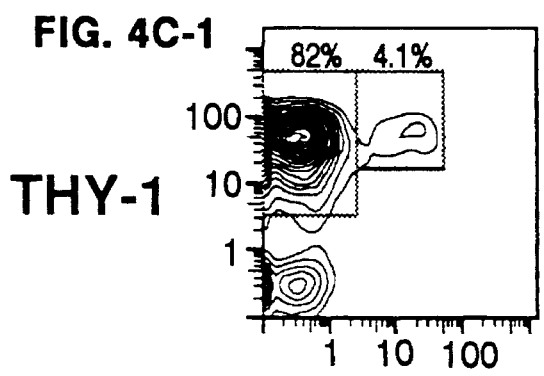
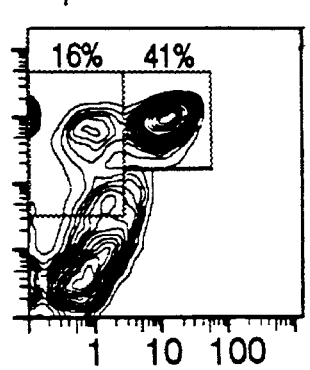
FIG. 4C-1  FIG. 4C-2

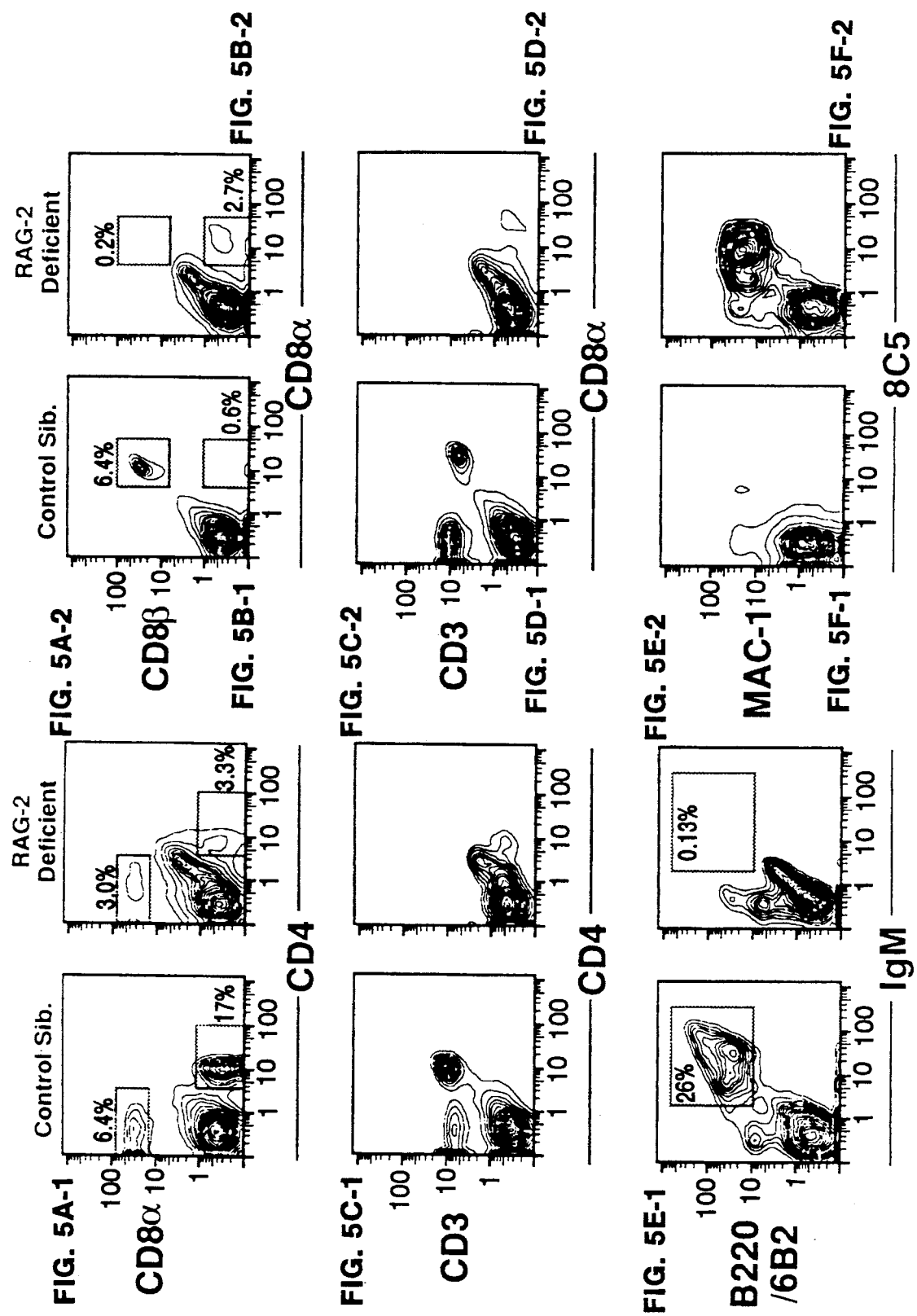

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

ACTTCAAGCT TCAGTTCTGG                                    20

RECOMBINATION ACTIVATING GENE DEFICIENT MOUSE

The invention disclosed herein was made with Government support under NIH Grant No. AI20047 from the Department of Health and Human Services. Accordingly, the U.S. Government has certain rights in this invention.

This is a continuation of application Ser. No. 07/847,565, filed Mar. 5, 1992, now abandoned.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

The lymphocytes within the vertebrate immune system recognize and respond to an enormous number of different antigens. Antigen recognition for B and T lymphocytes, respectively, is effected through the variable domains of immunoglobulin (Ig) or T cell receptor (TCR) molecules. Genes that encode these variable regions are assembled during the early stages of B and T lymphocyte differentiation from germline variable (V), diversity (D) and joining (J) gene segments by a process referred to as VDJ recombination. The enzymatic activity responsible for assembling these gene segments has been assayed within permanent precursor lymphoid cell lines through the use of recombination substrates that contained unrearranged V, D, or J segments plus selectable marker genes (reviewed by Blackwell and Alt, 1989). These types of assay demonstrated that the conserved recognition sequences (RS) that flank all antigen receptor variable region gene segments are sufficient to target VDJ recombinase assembles all antigen receptor gene segments (Yancopoulos, et al., 1986). In addition, assays of cell lines demonstrated that VDJ recombinase activity is expressed specifically in precursor (pre) B and T cells and not in non-lymphoid cells or in cells that represent more mature stages of the lymphocyte lineages (Blackwell, et al., 1986; Lieber, et al., 1987; Schatz and Baltimore, 1988).

Two genes that synergistically confer fibroblasts with ability to specifically rearrange transfected VDJ recombination substrates have been isolated and referred to as the recombination activating genes (RAG) 1 and 2 (Shatz, et al., 1989; Oettinger, et al., 1990). These two genes are evolutionarily conserved in vertebrates and closely linked in the chromosomes of mice, humans, and chickens (Shatz, et al., 1989; Oettinger, et al., 1990). The precise function of the RAG gene products has not been unequivocally elucidated, however, it is generally believed that they may encode the tissue specific components of the VDJ recombination system (Chun, et al., 1991). In the latter context, high level expression of the RAG-1 and RAG-2 genes has been found only in primary lymphocyte differentiation organs (eg. the thymus) and in cell lines that represent precursor stages of B and T cell development (Shatz, et al., 1989; Oettinger, et al., 1990). However, low level expression of RAG-1 and RAG-2 has been observed in a number of different organs (Chun, et al., 1991; Carlson, et al., 1991) fueling speculation that some type of site-specific recombination process may occur in other developmental processes.

The VDJ recombination process is believed to involve multiple activities, including recognition of the RS, endonucleolytic activity that site-specifically cleaves at the border of RS and adjacent gene segments, potential exonucleolytic and nucleotide-addition activities, polymerase activities, and ligase activity to join the free ends (reviewed by Blackwell and Alt, 1989 and Lewis and Gellert, 1989). Several of these activities, including RS recognition and cutting, are likely to involve lymphocyte specific activities, while others may reflect more generally expressed activities recruited by the lymphocyte specific components. A potential example of the latter is the activity encoded by the gene affected by the murine scid mutation (reviewed by Bosma and Carroll, 1991). Although mice homozygous for this mutation are impaired in the final, joining step of the VDJ recombination process (Malynn, et al., 1988; Lieber, et al., 1988; Blackwell, et al., 1989) resulting in the severe combined immune deficient (SCID) phenotype, the activity affected by the scid mutation appears to also be more generally involved in the DNA repair process (Fulop and Philips, 1990; Biedermann, et al., 1991., Hendrickson, et al., 1991).

Previous studies and applications using the SCID mice have been based on mice homozygous for the scid mutation (for general review, see McCune et al., 1989; Bosma and Carroll, 1991). Such scid mutated mice are severely deficient in functional B and T lymphocytes. The mutation appears to impair the recombination of antigen receptor genes and thereby causes an arrest in the early development of B and T lineage-committed cells; other hematopoietic cell types appear to develop and function normally.

One of the problems of scid mutated mice is that the arrest in lymphocyte development is not absolute; some young adult SCID mice are leaky and generate a few clones of functional B and T cells. By 10–14 months of age, virtually all SCID mice are leaky.

The recombination activating genes 1 and 2 (RAG-1 and 2) synergistically confer VDJ recombination activity to non-lymphoid cells. To assess RAG-2 gene function in normal physiology, we have deleted a large portion of the RAG-2 coding region in an embryonic stem cell line and used these cells to generate mice that harbor the mutation in their germline. Homozygous mutants are viable but fail to produce mature B or T lymphocytes even at several months of age. Very immature lymphoid cells were present in primary lymphoid organs of the homozygous mutants as defined by surface marker analyses and Abelson murine leukemia virus (A-MuLV) transformation assays. However, we could not detect rearrangements of immunoglobulin (Ig) or T cell receptor loci in cells of primary lymphoid organs or in homozygous mutant A-MuLV transformed pre-B cell lines. Lack of VDJ recombination activity in the mutant pre-B cell lines could be restored by introduction of a functional RAG-2 expression vector. Therefore, loss of RAG-2 function in vivo results in total inability to initiate VDJ rearrangement leading to a novel SCID phenotype. Furthermore, the SCID phenotype was the only obvious abnormality detected in RAG-2 mutant mice, indicating the VDJ recombinase activity, per se, is not required for development of cells other than lymphocytes.

SCID mice are susceptible to various infectious agents due to the absence of an effective immune system. SCID mice are highly susceptible to *Pneumocystis carinii*, an parasitic micro-organism which causes severe opportunistic infections in immune deficient humans, including HIV-1 infected humans (Roths et al., 1990). The SCID model should facilitate analysis of the factors determining *P. carinii* resistance, and it may provide a disease model in which therapeutic regimens can be tested.

Studies have shown that SCID mice are also susceptible to infections of spirochete *Borrelia burgdorferi*, which causes lyme borreliosis (Schaible et al., 1989). Such infections cause lyme arthritis and carditis. SCID is not only useful in propagating infective *B. burgdorferi*, it would be a good model for elucidating the role of cellular and humoral immune responses in the pathogenesis of lyme borreliosis. Different drugs or therapeutic protocols may be tested in this animal system.

Tumors can grow in SCID mice (summarized in Philips et al., 1989). Tumor tissues including retinoblastoma and osteogenic tumors, acute lymphoblastic leukemia, urologic malignant tumors, and human melanoma can grow in SCID mouse by engraftment. Depending on the types, tumors may be introduced intravenously, intraperitoneally or subcutaneously.

Human lung tumor growth has been established in the lung and subcutaneous tissue of SCID mice. The growth of a human lung tumor cell line may serve as a metastatic model in which to investigate patient lymphocyte tumor infiltration, and therapeutic and diagnostic efficacies of antitumor antibodies.

Human yolk sac tumor (YST-2) grew rapidly to enormous sizes in all SCID mice after both subcutaneous and intraperitoneal transplantation, while only half of the subcutaneous and none of the intraperitoneal transplants were accepted in usual athymic nude mice (Nomura, et al., 1990). Furthermore, transplanted tumors metastasized spontaneously to distant organs such as the lung, liver, kidney, pancreas, and spleen, in scid mutated mice, while metastases were not found in athymic nude mice. Similar results were observed in scid mutated mice and scid-nude double mutant mice with human classic seminoma which has been neither transplantable nor metastatic in athymic nude mice. Thus, SCID mice provide an invaluable experimental system for investigating the mechanism of metastasis, which is the most important and life-threatening problem in cancer patients.

Human germinal tumors were ectopically transplanted to SCID mice, and metastasis mimicking what were found in human were observed. It was also found that ectopically transplanted tumors spontaneously metastasized to distant organs in SCID mice but less frequently in leaky SCID mice, while metastasis has never been found in nude mice (Nomura T., et al., 1991).

SCID mice also provides an efficient and reproducible model to study the pathogenesis of children acute lymphoblastic leukemias and provides a suitable system for evaluating therapy. Upon intraperitoneal transfer, T cells from acute lymphoblastic leukemias spread hematogenously and infiltrate the non-lymphoid and/or lymphoid organs with a pattern reminiscent of the human clinical disease (Cesano et al., 1991).

The SCID mouse provides a useful in vivo model for evaluation of new therapeutic approaches for lymphoma treatment. Human cutaneous T-cell lymphoma has been established in SCID mice. In addition, primary human acute leukemia has been grown in SCID mice (DeLord et al., 1991).

Overall, the SCID mouse provides a useful in vivo model of human tumor establishment, progression, metastasis, and treatment.

SCID mice with defects in the maturation of T and B cells have provided a novel experimental system in which to study normal lymphoid differentiation and function in mouse and man (reviewed in McCune, J. M., 1991). A useful SCID-hu mouse is established by implanting human cells or tissues into the SCID mouse (reviewed in Mosier, D. E., 1990).

Via engraftment with human lymphoid progenitors, the SCID-hu mouse has been used to study infections of human lymphoid cells with the human immunodeficiency virus, HIV-1. The mouse may either first receive the engraftment of human lymphoid progenitors cells and subsequently be inoculated with the HIV virus or it may be engrafted directly with the virus-infected progenitor cells. The mouse may enable determination of how progressive infection occurs in defined CD4 lymphoid and myelomonocytic cell populations and may also be used to analyze the efficacy of antiviral drugs and vaccines, including the drug AZT. It has been shown that the animals were protected in dose ranges similar to those used in man. This animal model may now be used as an efficient intermediate step between the laboratory and the clinic to study the infectious process in vivo and to best select efficacious antiviral compounds against HIV (Kaneshima, et al., 1991).

Similarly, Epstein Bar Virus-related lymphoproliferative disorders can also be modeled by the transfer of adult peripheral blood mononuclear cell to SCID mice. Other viruses which can infect lymphocytes can be similarly studied. Once such a system is established, various kinds of drug and different schemes of treatment can be tested.

The SCID-hu mice have also been used to evaluate cytokine-induced killer cells with potent antitumor cell activity (Schmidt-Wolf, et al., 1991).

Fetal liver cells have been transplanted in SCID mice. Coimplantation of small fragments of human and fetal liver into immunodeficient SCID mice resulted in the formation of a unique structure (Thy/Liv). Thereafter, the SCID-hu mice showed reproducible and long-term reconstitution of human hematopoietic activity. For periods lasting 5–11 months after transplantation, active T lymphopoiesis was observed inside the grafts and cells that were negative for T cell markers were found to have colony-forming units for granulocyte/macrophage and erythroid burst-forming unit (BFU-E) activity.

The SCID-hu mouse can also be used in the analysis of the growth factors which regulate hematopoiesis (McCunne, et al., 1989). When fetal liver cells are administrated to the SCID-hu mouse intravenously in the absence of microenvironmental stromal cells and the growth factors they produce. The production of mature cells is time-limited. If human stem cells can be isolated, they will in turn serve as assays, either in vivo or in vitro, for the identification of those factors which regulate self-renewal and/or differentiation. This line of investigation has in the past been hampered for lack of a suitable assay. The SCID-hu mouse represents not only a means by which to purify stem cells and their progeny but also an assay system in which to monitor growth and differentiation.

It has been shown that bone marrow can be transplanted into SCID mice (Dorshkind, et al., 1989; Dorshkind, et al., 1986). The SCID mice have also been used as a model to identify and quantify myeloid and lymphoid stem cells (Fulop, G. M. 1989). SCID mice were also used to study the function of natural killer (NK) cells in bone marrow transplant (Murphy, W. J., 1989). SCID mouse contain normal NK cells and their progenitors and, therefore, provide a lymphoid-free system in which to study NK effector functions.

The feasibility of reconstitution of SCID mice with lymphocytes from normal mice and the possible engraftments with peripheral blood lymphocytes from other species render SCID mice ideal for assessing the importance of lymphocytes in control of pathogens, immune surveillance and reproduction.

Moreover, human and rat islet tissues have been transplanted to SCID-hu mice, and success has been observed (London, et al.,1991). Therefore, SCID-hu mice are useful in studying the effects of human immune response mediated by T and B lymphocyte against the islet tissue.

Though most of the above applications were done in scid mutated mice, it is an important objective of this invention that the RAG-2 deficient animal have an improved SCID phenotype and, therefore, the same application.

In scid mutated mice, leakiness may limit their applications. Scid mutated mice were first recognized as leaky on the basis of serum Ig in 2–25% of young adult mice (Bosma, et al., 1988). Though the molecular basis for the leaky SCID phenomenon is not yet clear, recent evidence suggests that leaky lymphocyte clones may reflect rare genetic events that enable a given SCID lymphoid progenitor and progeny to form a normal VDJ coding joint at normal frequency. A few clones of antigen receptor positive B and T lymphocytes do appear in a variable proportion of young adult SCID mice and in virtually all old SCID mice (Carroll et al., 1989; Carroll and Bosma 1988). As stated previously, some tumor implantations are not as successful because of this leakiness.

The recombinant RAG-2 deficient mice disclosed in this invention do not have any leaky phenotype and therefore are more advantageous than the scid mutated mice.

Another advantage of this invention is that RAG-2 mutation affects an earlier stage of VDJ recombination, and therefore, RAG-2 may be applied to areas which cannot be accommodated by scid mutated mice.

A third advantage may be that RAG-2 deficient mice appear to affect only lymphoid cells. The scid mutation has deleterious effects on general DNA repair mechanism and thus affect many different cell lineage.

Finally, scid mutated mice are generally difficult to propagate. To this point, RAG-2 deficient mice are able to propagate readily.

SUMMARY OF THE INVENTION

This invention features a recombinant non-human animal with both alleles of the recombination activating gene (RAG)-2 being functionally deficient. This recombinant non-human animal may be made by altering RAG-2. This invention provides that the alteration comprises addition, deletion or mutation of at least one nucleotide of a RAG-2 allele. This invention further provides that to make such deficiency, part or all of the RAG-2 can be deleted and replaced by at least one selectable marker gene. This invention further provides that the selectable marker genes include drug resistant genes, thymidine kinase gene, adenine phosphoribosyl transferase gene, hypoxanthineguanine phosphoribosyl transferase gene, neomycin resistant gene or a combination of more than one of the preceding genes.

This invention further provides that the VDJ recombinations of the lymphocytes is inhibited in the RAG-2 deficient non-human vertebrate animal. This invention provides that the lymphocytes of the homozygous RAG-2 deficient non-human vertebrate animal cannot reach maturity. This invention provides that the RAG-2 deficient non-human vertebrate animal may be any mammal.

This invention further provides a process to produce such a RAG-2 deficient animal. The process comprises modifying RAG-2 to render RAG-2 functionally deficient, introducing the modified RAG-2 into the genome of the animal, identifying the modified RAG-2 carrying animals and interbreeding of the modified RAG-2 carrying animal to generate RAG-2 deficient animal.

In an embodiment, RAG-2 is modified by insertion of a selection marker gene and a negatively selectable marker gene is then inserted adjacent to the modified RAG-2 whereby the distance between the marker gene and the modified RAG-2 is sufficient to carry out homologous recombination. This construct is introduced into embryonic stem cells and then positively select the marker which modifies the RAG-2 and negatively select for those that express the inserted adjacent marker. This positive and negative selection scheme will ensure that the modified RAG-2 will integrate to the correct locus in the genome of the animal. Our invention provides plasmid G3E2-12 which possess both the positive and negative marker for the introduction of the modified RAG-2 into embryonic stem cells. This invention further provides that the modified embryonic stem cells can be introduced by microinjection of the modified embryonic stem cell line to blastocyte of a developing embryo.

In an embodiment, this invention provides that the RAG-2 deficient animal comprises foreign organisms. In another embodiment, the homozygous RAG-2 deficient mutant animal comprises living cells. The living cells include islet cells, bone marrow cells, tumor cells and lymphocytes.

This invention also provides a method for growing foreign cells in the RAG-2 deficient animals. The foreign cells include islet cells, bone marrow cells, lymphocytes, infected lymphocytes, tumor cells, and various combinations of the above. The tumor cells may be derived from lymphoma, leukemia, lung tumors, melanoma, urologic malignant tumors, retinoblastoma, bladder tumors, prostate tumors, breast tumors, pancreatic carcinoma, renal cell tumors, osteogenic sarcoma, testicular tumors, human yolk sac tumors, human germinal tumors and Wilms' tumors.

This invention also provides a method of identifying and evaluating drugs, and evaluating different therapeutic protocols against infections, viral infections and tumors. The viral infections may be human immunodeficiency virus infections, cytomegalovirus infections, Herpes virus infections, other lymphotropic virus infections and hepatitis virus infections.

Finally, this invention provides a method to identify lymphokines and growth factors using the RAG-2 deficient animal.

BRIEF DESCRIPTION OF FIGURES

FIGS. 1A, 1B

Figures 6A, 6B:
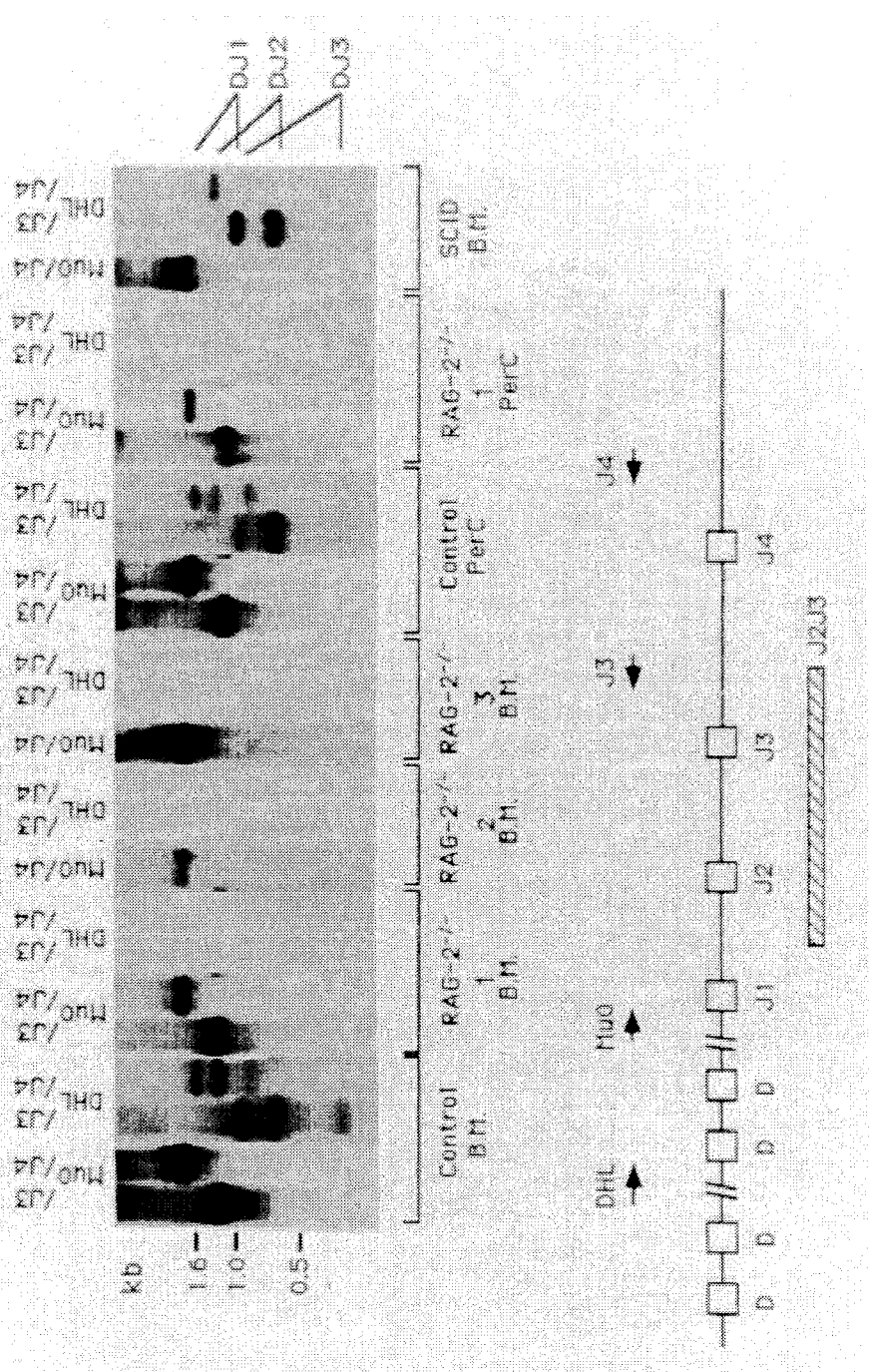

The Endogenous RAG Locus and the Targeting Construct for Homologous Recombination.

(A) Partial restriction endonuclease map of the RAG-2 locus. Bold lines represent introns, open boxes show exons of RAG genes and shaded boxes indicate coding regions of these genes. Arrows represent transcriptional orientation of the RAG genes.

(B) Design of the RAG-2 targeting construct, G3E2-12. This vector was constructed as described in Experimental Procedures. The PstI-PstI portion of the RAG-2 coding region was replaced with a 1.1 kb PMClneo/polyA$^+$ fragment (PMClNeopA$^+$). Thin lines represent plasmid sequences of KS pBluescript. Arrows indicate the transcriptional orientation of the HSV-tk and neo genes. Probes used in this study are shown under the targeting construct: probe A; SalI-XbaI 5' RAG-2 fragment, probe B; EcoRV-PstI RAG-2 fragment, probe C; PstI-PstI RAG-2 fragment, probe D; PstI-BamHI neogene fragment from PMClneo/polyA+. The expected sizes of restriction fragments detected by probe A and B are shown.

FIGS. 2A, 2B

Southern Blot Analysis of the RAG-2 Mutation in CCE cells. Ten μg of DNA from the parental CCE cells and appropriately targeted cell lines (B24 and B47) was digested with indicated restriction enzymes and assayed by Southern blotting methods for hybridization to probe A (A) or probe B (B). DNA from clone B24 shows additional fragments that hybridized weakly to probe B; this likely results from the B24 population being a mixture of two cell types—the majority containing the mutated RAG-2 allele and the other the result of a random integration event.

FIGS. 3A, 3B, 3C

Lack of Mature sIgM+B cells in Homozygous RAG-2 Mutant Mice. Bone marrow cells obtained from the two femurs of one-month old homozygous RAG-2 mutant mice ($1.4 \times 10^7$ cells recovered) and control littermates ($5.0 \times 10^7$ cells recovered) were analyzed by flow cytometry. Panel A: Cells were stained with $^{fl}$anti-IgM and $^{bi}$RA3-6B2, anti-B220 antibodies. The mature IgM+, B220+ B cells are noted in the hatched box. Panels B and C: the cells were simultaneously stained with $^{fl}$S7, anti-CD43, $^{PE}$anti-BP-1, $^{APC}$6B2 (anti-B220) and $^{bi}$30Fl (anti-heat stable antigen). Biotin conjugated reagents were revealed by TR-Avidin. B Panels show the CD43 vs B220 contour plots. Contour plots for 30Fl v. BP-1 is shown for B220+, CD43+ cells (Panel C). The gates used for Panel C are shown in Panel B. Pro-B fractions a, b, and c (as described by Hardy et al., 1991; see text for details) are indicated in panel C.

FIGS. 4A, 4B, 4C

Thymocytes from RAG-2 Mutant Mice Lack T Cell Receptor Positive T cells. Thymocytes from RAG-2 mutant mice ($5.1 \times 10^6$ cells recovered) and control siblings ($1.5 \times 10^8$ cells recovered) were examined for CD4 and CD8 expression (Panel A), TCR αβ and TCRγδ populations (Panel B) and Thy-1 and IL-2Re (Panel C). The cells were stained with the following combinations of antibodies: $^{fl\ anti-CD}$4 and $^{fl}$anti-CD8; flanti-TCRβ and $^{bi}$anti-TCRδ; antiIL-2Rα and $^{bi}$antiThy-1. The percentage of cells staining for a particular phenotype are indicated in the various boxed regions.

FIGS. 5A, 5B, 5C, 5D, 5E, 5F

Analysis of Splenocytes from RAG-2 Mutant Mice. The presence of various splenic hematopoetic cell populations was examined in RAG-2 mutant mice ($8.2 \times 10^6$ cells recovered) and control siblings ($3.0 \times 10^7$ cells recovered). The T cell compartment was analyzed by simultaneously stained with either $^{fl}$anti-CD3, $^{APC}$anti-CD4 and $^{bi}$anti-CD8α (Lyte-2) antibodies; or $^{fl}$anti-CD8α (Lyte-2) and $^{bi}$anti-CD8β (Lyt-3). For the analysis of the B cell compartment, cells were stained as described in FIG. 3 with anti-IgM and anti-B220 antibodies (lower left panel). Myeloidlineage cells were revealed with $^{fl}$8C5, anti-Gr-1 and $^{bi}$anti-Mac-1 antibodies in a separate staining experiment. The percentages of cells positive for a given phenotype are indicated in the boxed region.

FIG. 6

Absence of Igh J to Rearrangements in Mice Homozygous for the RAG-2 Mutation. Cell lysates were prepared from bone marrow cells (B. M.) and peritoneal washout cells (PerC) of control, homozygous mutant (RAG-2$^{-/-}$ and Scid mice. IgH $D_H$ to $J_H$ recombination gene products were analyzed by PCR from these cell lysates using a combination of degenerate $D_H$(DHL) and $J_H3$ (J3) or $J_H4$ primers as described by Schlissel et al., (1991). The PCR-amplified products were fractionated on agarose gels and assayed for hybridization to a $J_H2$–$J_H3$ probe (J2J3) by Southern blotting methods. A primer 5' of $J_H1$ (MuO) was used as an internal control for the PCR. Sizes of the expected PCR products hybridizing to the $J_H$ probe are: ~987(DJ1), ~599(DJ2) and ~274(DJ3)bp with the DHL/J3 primers combination; ~1591(DJ1), ~1272(DJ2) and ~887(DJ3)bp with the DHL/J4 primers combination; and 1282(MuO/J4)bp and 1895 (MuO/J4)bp.

FIG. 7

Germ-Line Configuration of TCRβ and TCRδ Genes on RAG-2 Mutant Thymocytes. Ten μg of EcoRI or HindIII restricted DNA from the indicated sources was assayed by Southern blotting procedures for hybridization to probes that specifically detect rearrangements of the TCRB (pDβ1.1; Siu et al., 1984) or TCRδ(p3'Jδ1; Chien et al., 1987 ) loci.

FIG. 8

Germ-line Configuration of the $J_H$ Locus in A-MuLV-transformed Pre-B lines Homozygous for the RAG-2 Mutation. Ten μg of EcoRI-restricted DNA from A-MuLV-transformed fetal liver cell lines homozygous (63 series) and heterozygous (64 and 65 series) for the RAG-2 mutation were analyzed by Southern blotting procedures for hybridization to a $J_H$-specific DNA probe.

FIG. 9

Gene Expression in A-MuLV-transformed Cell Lines. Ten μg of RNA from the indicated sources was analyzed by Northern blotting procedures for hybridization to a series of different probes including: RAG-1 (a 1.4 kb RAG-1 fragment, Schatz et al., 1989); RAG-2 (complete RAG-2 cDNA; Oettinger et al., 1990); Cμ (Bothwell et al., 1981), the pre-B cell specific gene λ5 (full length cDNA, Yancopoulos et al., 1991) and the housekeeping gene GAPDH (Fort et al., 1985).

FIG. 10

Vector for use in eliminating the function of the RAG-1 gene.

DETAILED DESCRIPTION OF THE INVENTION

This invention relates to a recombinant, non-human vertebrate animal which comprises functionally deficient RAG-2. The Functional deficiency describing the RAG-2, may occur in the DNA, RNA or protein level such that the functional gene product of RAG-2 is either not produced or deficient. One of the phenotype of such deficiency is characterized by the substantial depletion of mature lymphocytes.

In a preferred embodiment, such a deficiency is created by altering a RAG-2 at DNA level. The alteration is to inactivate the RAG-2 and stop the RAG-2 gene expression. The alteration can be an addition, deletion, mutation or any combination of these three methods. More than one nucleotide may be added or deleted from RAG-2, and more than one nucleotide may be mutated.

An embodiment of this invention is the deletion of part or all of RAG-2 DNA and the replacement by at least one selectable marker gene. The selectable marker genes include but are not limited to neomycin resistant gene, thymidine kinase gene, adenine phosphoribosyl transferase gene, hypoxanthine-guanine phosphoribosyl transferase gene, dihydrofolate reductase gene or a combination of more than one of the preceding genes or other selectable marker genes known to an ordinary skilled in the art. These selectable marker genes will express particular phenotypes under appropriate selective conditions.

In an embodiment, the recombinant non-human vertebrate animal of this invention is generated by deleting part or all of the coding region of RAG-2 and replaced by neomycin resistant gene.

Alternatively, antisense DNA or RNA which can hybridize with RAG-2 DNA may be introduced into the animal to hybridize with the RAG-2 mRNA such that substantial translation cannot occur and therefore, much reduced amount of functional protein is produced. The method of introduction of the antisense DNA or RNA into the cell is known to a skilled practitioner. One method is to clone and express an antisense RAG-2 under a strong promoter such that large amount of antisense RNA against RAG-2 will be produced. The antisense RAG-2 RNA produced will hybridize with the normal RAG-2 mRNA and therefore, interfering with the expression of RAG-2.

Another alternative is to engineering an early stop codon into the gene such that only nonfunctional truncated RAG-2 protein will be produced.

The VDJ recombinations in the lymphocytes of the RAG-2 deficient animal are deficient, and the lymphocytes of the said animal cannot reach maturity, resulting in the SCID phenotype.

Although the experiments discussed hereinafter concern a recombinant RAG-2 deficient mouse, it is clear that the recombinant animals of this invention may be of any vertebrate species which have recombination activating gene-2. As we have noted before, RAG-2 have been found in different species (Shatz et al., 1989; Oettinger et al., 1990). Therefore, it is to be understood that the invention encompasses all vertebrate animals.

Another aspect of the invention involves a process to produce a recombinant RAG-2 deficient non-human vertebrate animal. Generally, such animal is produced by a) modification of RAG-2 so that the RAG-2 gene product is functionally deficient, b) introduction of the modified RAG2 into the genome of the animal, c) identify the modified RAG-2 carrying animals; and d) generating the modified RAG-2 carrying animal which is RAG-2 deficient.

The modification of RAG-2 comprises addition, deletion or mutation, or any other method known to ordinary skilled in the art. Alternatively, the DNA of RAG-2 may be modified by methylation or the like to inactivate the gene expression.

In a preferred embodiment, the RAG-2 is cloned in a plasmid and the modification of RAG-2 is done on the cloned RAG-2 DNA. Various plasmids well known to a skilled practitioner will serve this purpose. In another preferred embodiment, the modification of RAG-2 is a partial deletion of the coding region and an insertion of a selectable marker gene.

Various drug resistance genes are examples of selectable marker genes. Some of the drug resistant genes are neomycin resistant gene and dihydrofolate reductase which can be selected by methotrexate. Other selectable marker genes include thymidine kinase gene, adenins phosphoribosyl transferass gene, hypoxanthine-guanine phosphoribosyl transferase gene. In a preferred embodiment, neomycin resistance gene is used for selection and to modified RAG-2.

The introduction of the modified gene to the genome of the animal comprises microinjection of the modified RAG-2 into the mouse egg or embryo; electroporation of the modified RAG-2 into the mouse egg or embryo or other techniques of introduction known to an ordinary skilled in the art.

In some situations, embryonic stem cells are cultured in vitro and introduced into the blastocytes. Modified RAG-2 may be introduced to the animal by the embryonic stem cell.

In a preferred embodiment, RAG-2 is isolated and cloned in a cloning vehicle. Such vehicle may be a plasmid, bacteriophage, other virus or the like known to the ordinary skilled in the art. The clone RAG-2 is then modified by insertion of a selection marker gene. A negatively selectable marker gene is then inserted adjacent to the modified RAG-2 whereby the distance between the marker gene and the modified RAG-2 is sufficient to carry out homologous recombination. The plasmid containing the modified gene is used to transform an embryonic stem cell line. The cells which incorporate the modified RAG-2 are positively selected for the marker in RAG-2 locus and negatively selected for the inserted adjacent marker. The final selected modified embryonic stem cell line is microinjected into the blastocyte of a developing embryo. Alternatively, the plasmid containing modified RAG-2 with the selection marker gene transforms stem cells directly and the transformed stem cells are selected for the selection marker phenotype.

In an embodiment, a modified RAG-2 is cloned into a plasmid, called G3E-12. G3E-12 is shown in figure i(B), in which part of the coding region of RAG-2 is deleted and a selection marker neomycin resistant gene is inserted at RAG-2. A negative selection marker, the thymidine kinase gene is constructed next to this new construct. This plasmid is transfected into the embryonic stem cells. The transfected stem cells are then positively selected with the expression of neomycin resistance phenotype and negatively selected with thymidine kinase phenotype.

In a preferred embodiment to generate RAG-2 deficient mouse, a mouse embryonic line, CCE of the mouse system is transfected by the modified mouse RAG-2. A stable modified mouse embryonic stem cell line generated by transfection of G3E-12, selected by the positive and negative scheme described above is called B47.

The plasmid, G3E-12 and the modified mouse embryonic stem cell line, B47 were deposited with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. G3E-12 was accorded ATCC designation number 75198 and B47 was accorded ATCC designation number ATCC CRL 10971.

In an embodiment, the modified mouse embryonic stem cell line is microinjected to blastocyte of a developing mouse embryo. Cell line, B47 which is transformed by G3E-12, is microinjected into the blastocyst of a mouse embryo to generate RAG-2 deficient mouse.

The invention's RAG-2 deficient animals are susceptible to various infections, particularly opportunistic infections owing to the SCID phenotype.

Such infections include bacterial infections, vital infections, protozoic infections, fungal infections, parasitic infections, other opportunistic infections and the like. The infection can be spirochete *Borrelia burgdorferi* or *Pheumocystis carinii* which have been shown to infect the scid mutated mice.

Infectious agents may be administered to the RAG-2 deficient animal orally, intravenously (iv), intraperitoneally (ip), subcutaneously (sc) or via like routes known to an ordinary skilled practitioner.

Evidence of successful infection may be manifested by the symptoms generated by the administered animals. If the infection is asymptomatic, tests may be done to test the amount of infectious agent present in the administered animal. An increase in the amount will show that the agent is replicating, and the infection is established. To some chronic infections, the infected cells may be examined to determine whether the infection is established or not. The methods for administration of infection and the establishment of an infection is well known to an ordinary skilled in the art.

The infected animals are useful in identifying drugs against various infections. New drug can be tested in this infected RAG-2 deficient animal, and various known drugs can be administered to the infected animal to test their efficacies to a specific infection. Multiple infections can be set up in the RAG-2 deficient animal to test the effect of treatment. For example, sequential infections, such as a viral infection followed by a bacterial infection are quite common in patients. The RAG-2 deficient animal may be sequentially infected to mimic the clinical infection pattern and test the efficacy of various treatments. Different therapeutic protocols can also be evaluated similarly.

One way to monitor the effect of treatment on the infected animal is to test the amount of infectious agents left in the treated animals. The blood in treated animals may be extracted and tested. A decline in the amount of infectious agent compared with the control untreated infected animal will indicate that the drug has certain inhibitory effects on the infectious agent. Alternatively, the recovery time of the treated animal and the untreated animal may be compared. The shorter the time required for recovery, the more effective the drug.

Another aspect of the invention relates to growing different foreign cells in the RAG-2 deficient animal. Since RAG-2 deficient animals do not have mature B or T lymphocytes, foreign cells or antigens derived either from the same species or different species can remain in such animals for a relatively long time without much attacks from the animal's immune system. Various animal cells including islet cells, bone marrow cells, tumor cells and lymphocytes may be cultured in RAG-2 deficient animals.

Methods of administering such foreign cells to RAG-2 deficient animals are well known to a skilled practitioner. Cells may be administered to RAG-2 animals iv, ip, sc or via like routes known to an ordinary skilled practitioner. Alternatively, tissues containing cells of interest can be transplanted into the animal ip, sc or directly into the different animal organs.

The RAG-2 deficient animal is useful for growing different tumors. Tumor cells can be transplanted ip, iv, sc or via routes known to ordinary skilled in the art. Alternatively, tumor tissues can be implanted in RAG-2 deficient animals. Examples of tumors are lymphoma, leukemia, lung tumors, melanoma, ufologic malignant tumors, retinoblastoma, bladder tumors, prostate tumors, breast tumors, pancreatic carcinoma, renal cell tumors, osteogenic sarcoma, testicular tumors, human yold sac tumors, human germinal tumors and Wilms' tumors.

Potential drugs or known drugs may be administered to the transplanted animals and the efficacy of such drugs could be evaluated. Also, different treatment protocols can be tested in the transplanted animals.

In another embodiment of the invention, lymphocytes are transplanted to RAG-2 deficient animals. The transplanted lymphocytes will grow and proliferate in the animals. Such animals are useful for identification and evaluation of lymphokine. Potential lymphokine may be administered to the animals and the proliferation of different subpopulations of lymphocytes will be monitored. The results will show whether the activities of the tested lymphokine and its effect on different subpopulations of lymphocytes. Similarly, the activities of different lymphokines can be assayed in such lymphocyte transplanted animals.

In another embodiment, such transplanted lymphocytes are secreting antibodies. The secreted antibodies can be harvested and purified from the blood of the animal. In a preferred embodiment, the antibodies secreting lymphocytes are derived from human and therefore, producing human antibodies.

RAG-2 deficient animals are also useful in growing or propagating lymphocytes infected with at least one infectious agent. The infectious agents may be viruses such as human immunodeficiency viruses, cytomegaloviruses, Herpes viruses, Epstein Barr viruses, other lymphotrophic viruses, Hepatitis viruses and the like which can infected lymphocytes. The RAG-2 mouse propagated with infected lymphocytes is useful for identifying potentially useful drugs or evaluating different known drugs against the viral infection.

In one embodiment, RAG-2 deficient animals are useful in identifying or evaluating drugs against acquired immunodeficiency syndrome (AIDS). The animals can either first receive the engraftment of human lymphoid progenitors cells and subsequently be inoculated with the HIV virus or can be engrafted directly with the virus-infected progenitor cells. The animals are useful in determining how progressive infection occurs in defined CD4 lymphold and myelomonocytic cell populations and analyzing the efficacy of antiviral drugs and vaccines, including the drug AZT. The RAG-2 deficient animal is an efficient intermediate step between the laboratory and the clinic to study the infectious process in vivo and to best select efficacious antiviral compounds against HIV.

RAG-2 deficient animals are useful in growing bone marrow cells. The established transplanted animals are useful in identifying growth factors which regulate hematopoiesis. Such potential growth factors may be administered to the transplanted animals to evaluate their activities to regulate hematopoiesis. The transplanted animals will further be useful to evaluate the activities or therapeutic value of the known hematopoiesis growth factor.

It is clear that one need both RAG-2 and RAG-1 to accomplish VDJ recombination. Therefore, one could also make a SCID animal by abolishing the function of the RAG-1 gene. Such an animal would be predicted to have a phenotype similar to that of the RAG-2 deficient animal and its uses should be identical assuming that it also has no defects outside of those involving the development of lymphocytes.

Figure 10:
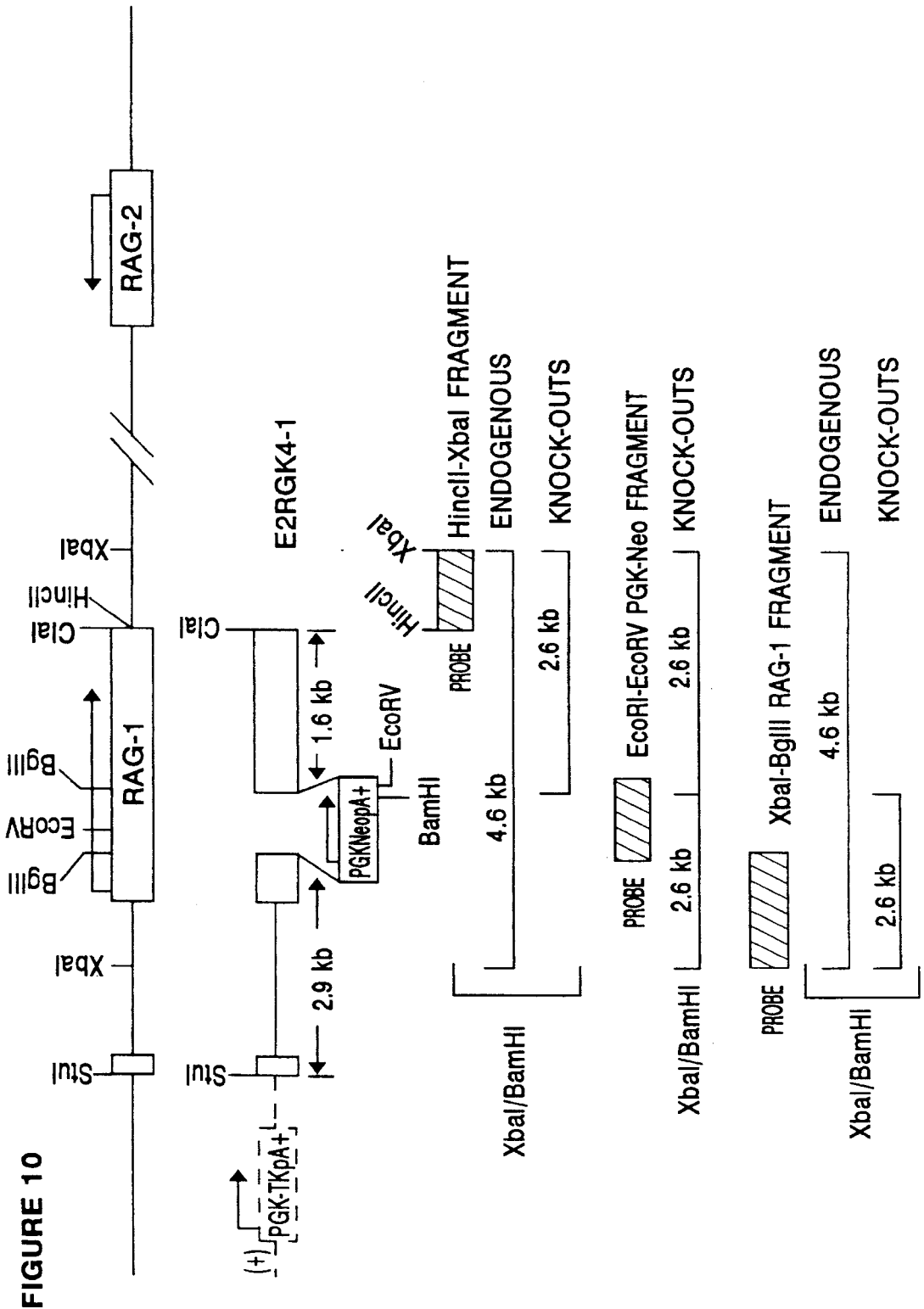

In an embodiment, the construction of a RAG-1 deficient mouse is accomplished by methods identical to those described for the construction of a RAG-2 deficient mouse. An appropriate vector for use in eliminating the function of the RAG-1 gene is outline in FIG. 10. This vector has already been used to create embryonic stem cells in which one copy of the RAG-1 gene is disrupted. These RAG-1 mutant stem cells have been used to make chimetic mice which are currently being bred to introduce the mutation into the germline as described for the RAG-2 deficient mice.

This invention will be better understood from the Experimental Details which follow. However, one skilled in the art

Experimental Details

Experimental procedures

Vector Construction: A 4.0 kb SalI-XbaI genomic DNA fragment containing the RAG-2 gene was isolated from a genomic lambda phage clone carrying the RAG-2 gene and subcloned into KS pBluescript (Stratagene). A 0.85 kb PstI fragment containing part of the RAG-2 coding region was replaced with a 1.1 kb XhoI-BamHI PMCl-neo/polyA$^+$ fragment (Stratagene). The mutated RAG-2 fragment was then subcloned into the KS pBluescript containing a 2.7 kb EcoRI-HindIII PGK-HSVtk fragment of pKJ-1. The final construct G3E2-12 (FIG. 1) was linearized with XhoI and used for ES cell transfections.

Transfection and Screenina of RAG-2 Mutant ES Cell Clone: 20 μg of linearized G3E2-12 was transfected into $2 \times 10^7$ ES cells, (CCE) as described (Schwartzberg et al., 1990). Transfected clones were selected with G418 (0.4 mg/ml) and Ganciclovir (1 μM), and resistant colonies were picked at day 9 after the transfection. RAG-2 mutant clones were identified by Southern blot screening (as described in the text).

Establishment of RAG-2 Mutant Mouse: ES cell clones containing one mutated RAG-2 allele were injected into blastocysts of C57BL/6 or MF1 mice and transplanted into uteri of foster mothers. Male chimera were mated with MF1 females and germline transmission of an ES cell gene background judged by the eye and/or coat color of offspring. Mice homozygous for the mutated RAG-2 gene were generated by crossing mice heterozygous for the mutated gene. Offspring homozygous or heterozygous for the mutation were determined by slot blot analysis of the tail DNA using a combination of probes specific for the mutated allele (neo probe C) and the endogenous allele (probe D) (FIG. 1B).

Flow Cytometry Analysis: Single cell suspensions from bone marrow, spleen and thymus and peritoneal washout cells of mice from 2 days to 2 months of age were prepared by standard methods as described (Parks etal., 1986). At least 10 individual animals were assayed for every analysis shown; because the data was essentially identical within every set of control animals or within every set of mutant animals, results from only one animal are shown on the various figures. Prepared cells were strained with fluorescein (fl), alophycoerythrin (APC) or biotin (bi) conjugated monoclonal antibodies as noted in the text. Biotin conjugates were revealed by phycoerythrinstreptavidin (PE-avidin, Southern Biotechnology) or texas red-streptavidin (TR-avidin). Dead cells were excluded by staining with propidium iodide. All analyses were carried out using a FACStar$^{Plus}$ (Becton-Dickinson). The data were analyzed using FACS-DESK software (Stanford University) and are presented as 5% probability contour plots.

The following monoclonal antibodies used in this study were purified and conjugated in our labs: RA3-6B2 (B220 [CD45R]); 331 (IgM); 11–26 (IgD); M1/70 (Mac-1); GK1.5 (CD4); 53-6 (CD8α [Lyt-2]); and 53-5 (CD8β [Lyt3]). The following antibodies were obtained from Pharmingen, San Diego, Calif.: 53-2 (Thy-1.2); 145-2C11 (CD3ε); 7D4 (IL-2Rα); RB6-8C5 (Gr-1); H57-597 (TCRβ); GL3 (RCRδ). The S7 (CD43), 30 Fl (Heat Stable Antigen) and BP-1 antibodies were generously provided by Dr. R. R. Hardy, Fox Chase Cancer Center, Philadelphia.

Cytotoxicity assay: NK-mediated target cytolysis was examined by a standard $^{51}$Cr-release assay. Effector cells were prepared from spleen 24 h after poly I-C intraperitoneal injection (100 μg/mouse). Various quantities of the effector cells and $1 \times 10^4$ $^{51}$Cr-labeled target cells (YAC-1) were mixed in 200 μl culture medium, pleated in round-bottom 96-well plate, and incubated at 37° C. for 4 h. After incubation, half of the supernatant of each well was collected for determination of radioactivity. The percentage of specific $^{51}$Cr release was calculated from the formula, 100× (X–Y)/(Z∝Y), where X is $^{51}$Cr release in the presence of effector cells, Y is the spontaneous $^{51}$Cr release in the absence of effector cells, and Z is the total $^{51}$Cr release from target cells with 0.5% Triton X-100.

PCR Assays: Preparation of cell lysates and PCR for Igh D to J rearrangements were performed as described (Schlissel et al., 1991) except for substituting a $J_H 3$ primer (J3): ACTTCAAGCTTCAGTTCTGG. The sizes of the expected PCR products are described in the legend to FIG. 6.

Transient Expression. Assay of Recombinase Activity:

Transient expression of recombinase activity in the RAG-2$^{-/-}$ and RAG-2$^{+/-}$ A-MuLV-transformants was assayed as described (Hesse et al., 1987). Briefly, approximately $3 \times 10^6$ cells were transfected with 200 ng of the recombination substrate pJH200 and 3 μg of RAG-1 (PDRI) or RAG-2 (PDRII) expression constructs driven by a $V_H$ promoter/IgH enhancer combination that will be described in detail elsewhere (Rathbun, Oltz, and Alt, unpublished data). After 48 h of culture, plasmids were recovered by an alkaline lysis procedure, digested with DpnI to delete plasmids that had not undergone replication in the cell lines, and introduced into E. coli strain MC1061 by electroporation. The transformed bacteria were selected by Amp (100 μg/ml) or Amp/Cam(10 μg/ml) and antibiotic resistant colonies were counted 24 h after the selection. The percentage of recombinants, R, is calculated from the formula, 100×the number of Amp$^R$/Cam$^R$ colonies/the number of Amp$^R$ colonies. As a control, plasmids of some drug resistant colonies were analyzed for appropriate rearrangements by HindIII digestion.

Southern and Northern Blot Analysis. DNA, RNA or PCR amplified DNA were separated on an agarose gel as described (Yancopoulos et al, 1986), transferred to Zetaprobe membrane (BioRad) and hybridized with probes labeled by random hexamer labelling with [a-$^{32}$P]dCTP.

Experimental Results

Targeting of the RAG-2 Gene and Generation of Mice Homozygous for the Mutation

The putative RAG-2 protein is encoded within a single exon (Oettinger, et al., 1990; FIG. 1A). To target disruption of the RAG-2 gene, we employed the positive/negative selection strategy (Mansour et al., 1988) using the G3E2-12 vector (FIG. 1B). Briefly, this construct was prepared by the excision of a 0.85 kb segment of the RAG-2 open reading frame from a 4.0 kb RAG-2 genomic DNA lambda phage clone and its replacement with the PMClneo gene which provides for positive selection. This replacement eliminates the potential to encode 286 of the 527 amino acids of the putative RAG-2 protein and also should not permit translation of the remaining downstream RAG-2 open reading frame. In addition, the herpes simplex virus thymidine kinase (HSV-tk) gene, driven by the phosphoglycerate kinase-1 (PGK) promoter, was incorporated into the plasmid region of the targeting vector to allow negative selection (by plating in ganciclovir) against random integration events. The G3E2-12 construct was transfected into CCE line of ES cells followed by isolation G418$^R$ and ganciclovir (GANC)$^R$ colonies. From $1.5 \times 10^7$ transfected CCE cells, approximately 1000 G418$^R$ colonies were isolated and, of these, approximately 100 were also resistant to GANC. We prepared genomic DNA from individual double resistant colonies and screened for homologous recombination events between the G3E2-12 construct and the endogenous RAG-2 gene by Southern blotting methods. For this purpose, EcoRI plus XbaI digested DNA was assayed for hybridization to a probe from the 5' portion of the genomic RAG-2 gene (Probe A, FIG. 1B). These analyses indicated that 3 of 65 G418R/ GANC$^R$ clones screened contained a replacement of one of the two RAG-2 loci by the G3E2-12 targeting construct (FIG. 2; two positive clones are shown.) From this result, the average frequency of homologous recombination was about 1 in 20 G418$^{R/GANCR}$ clones which implies an overall targeting efficiency of approximately 1 in 250 G418$^R$ clones.

We characterized the integration events in detail from two clones (B24 and B47) that appeared to contain homologous integration events based on the preliminary analyses described above (FIG. 2). Based on analyses with a variety of restriction digests and probes, DNA from both clones contained a single copy of the various hybridizing fragments predicted for the endogenous and mutated allele (diagrammed in FIG. 1B). Southern blot analysis using a Y chromosome-specific probe demonstrated that both of these clones had the same pattern of restriction fragments as parental CCE ES cell line (data not shown). In addition, karyotypic analyses confirmed that the majority of cells within these clones had 40 chromosomes (data not shown). Clone B47 was injected into 3.5 day old C57BL/6 or MF1 blastocysts and chimeric mice were obtained. Male chimeric mice were bred to test for germline transmission of the mutated RAG-2 gene. From 15 males screened, 5 have yielded germline transmission and 3 of these 5 gave 100% transmission.

Mice heterozygous for the mutated RAG-2 allele did not show any detectable phenotype compared to wild-type littermates; hereafter, we will refer to both types of mice as "control" animals in cases where we have not distinguished whether they are heterozygous or wild-type. To further test transmission, heterozygotes were bred with each other. Based on tail DNA analyses of 130 progeny generated by intercrossing the heterozygous mice, wild-type (RAG-2$^{+/+}$), heterozygous (RAG-2$^{+/-}$) and homozygous mutant (RAG-2$^{-/-}$) mice was approximately 1:2:1. Therefore, disruption of the RAG-2 gene does not result in embryonic lethality. Neonatal RAG-2$^{-/-}$ mice were healthy and had no gross abnormalities (see below), but when maintained in non-barrier facilities for several months they generally were smaller in size than heterozygous littermates and routinely developed infections.

Analysis of the Immune System of Mutant Mice

Given the predisposition of the mutant animals to infections and the known relationship of the RAG-2 gene to the VDJ recombination process, we examined the effect of the RAG-2 mutation on the immune system. Gross inspection of the lymphoid organs of homozygous mutant mice showed that the mutant thymus was exceptionally small or, occasionally, absent. The number of cells in thymus of RAG-2$^{-/-}$ mice ranged from 10 to more than 100 fold less than that of RAG-2$^{+/-}$ or RAG-2$^{+/+}$ littermates with the differences becoming more dramatic as the mice aged. The spleens of homozygous mutant animals were physically comparable in size to those of heterozygous or wild-type animals (except for sick animals), but had 5–10 times fewer cells compared to those of control littermates.

Defective B Cell Development in Homozygous RAG-2 Mutants

B cell development is a highly ordered process in which progenitor cells undergo sequential differentiation steps that have been defined by the expression of stage-specific cell surface markers (reviewed by Rolink and Melchers, 1991). Mature B cells have rearranged both Ig heavy and light chain genes and express complete Ig molecules on their surface (sIgM) as well as a relatively high level of the B lineage-specific B220 surface marker (CD45R). Immature B cell precursors (pro-B or Pre-B cells) do not express sIgM but can be identified by the low level expression of B220. Cells that express sIgM are readily apparent in the bone marrow of one month old control animals but strikingly absent from RAG-2$^{-/-}$ littermates (FIG. 3A and data not shown). Furthermore, no sIgM$^+$ cells were detectable in the spleen (FIG. 5E) or in peritoneal washout cells (not shown) of homozygous mutant mice. Correspondingly, we also did not detect any IgM in the serum of RAG-2$^{-/-}$ mice by sensitive ELISA assays (data not shown). Although lacking in mature sIgM$^+$ cells, RAG-2$^{-/-}$ mutant mice had substantial numbers of sIgM$^-$/B220$^{dull}$ B lineage cells in the bone marrow (FIG. 3A) and spleen (FIG. 5E). Together, these results indicate that the homozygous RAG-2 mutation leads to a complete block in B cell differentiation, probably at an early B cell differentiation, probably at an early B cell progenitor stage.

In normal mice, the sIgM$^-$/B220$^{dull}$ populations include pro-B cells which have not yet initiated the Ig gene rearrangement process and pre-B cells that have rearranged and expressed their Ig heavy chain but not light chain genes. To further elucidate the stage at which B cell development is blocked, we assayed bone marrow cells from mutant and normal animals for expression of surface markers (CD43, BP-1, and 30F1) that resolve B cell progenitors into discrete stages (Hardy, et al., 1991). In normal mouse bone marrow, the B220$^+$/CD43$^-$ population consists of pre-B cells and mature sIg$^+$ B cells, whereas the B220$^{dull/CD}$43$^+$ population contains more immature B lineage cells. In contrast to normal mice, nearly all bone marrow B220$^{dull}$ cells in RAG-2$^{-/-}$ mice are also CD43+ indicating that B cell development is blocked at an immature stage (FIG. 3B). However, it should be noted that while the B220$^{dull/CD}$43$^+$ cells comprise a larger percentage of the homozygous RAG-2 mutant bone marrow compared to that of control mice (FIG. 3B), this population is present in similar absolute numbers in both (data not shown).

The B220$^{dull}$/CD43$^+$ phase of B cell development has been further divided into populations that lack detectable J$_H$ rearrangements (Fraction A cells; 30F1$^-$/BP-1$^-$), a population in which cells contain either germline J$_H$ loci or DJ$_H$ rearrangements (Fraction B; 30F1$^{dull}$, BP-1$^-$) and a population in which most cells have undergone J$_H$ rearrangements (Fraction C; 30F1$^+$/BP-1$^+$) (Hardy, et al., 1991). The great majority of bone marrow B lineage cells in RAG-2$^{-/-}$ mutant mice express the Fraction B phenotype (FIG. 3C). Thus, B cell development appears to be arrested precisely at the developmental point at which Ig gene rearrangement is initiated in normal mice. Similar to the homozygous RAG-2 mutant animals, the vast majority of B lineage cells in the bone marrow of scid mice are also B220$^{dull}$/CD43$^+$ (Hardy, et al., 1989). However, the scid mice have higher numbers of fraction A and C cells than the RAG-2 mutants (R. R. Hardy, personal communication). This may reflect a difference in the precise stage at which these two defects abort B cell development but also may reflect differences in the backgrounds of the mutant mouse lines analyzed.

Defective T Cell Development in Homozygous RAG-2 Mutant Mice

T lymphocyte differentiation in the thymus generally proceeds from null cells to CD4$^+$CD8$^+$ (double positive) cells and then to cells that express either CD4 or CD8 alone (single positive cells). The latter cells of mature phenotype also express the T cell antigen receptor (TCR) and the associated CD3 polypeptide complex (reviewed by Finkel et al., 1991). We could not detect either double or single positive cells in thymuses from RAG-2$^{-/-}$ mice between 1 day to two months of age (FIG. 4A; one month old mice). This block in T cell development was further confirmed by our inability to detect cells that express TCRαβ or TCRγδ (FIG. 4B). We also failed to detect CD3$^+$ populations in the thymuses or spleen the RAG-2$^{-/-}$ mice, confirming the lack of mature T cells (FIG. 5C, D, and data not shown). However, a small population of CD8 single positive splenocytes was observed in all RAG-2$^{-/-}$ mice analyzed (FIG. 5A), and a small CD4 single positive splenocytes was observed in some RAG-2$^{-/-}$ animals (FIG. 5A). These single positive cells did not express detectable levels of the TCR or its associated CD3 molecule indicating that they did not represent a known T cell subset (FIG. 5C and D). In addition, the CD8$^+$ single positive cells expressed only the CD8α chain, in the absence of the CD8β chain (FIG. 4B). Because approximately one third of the human natural killer (NK) cell population expresses CD8α but not CD8β chains (H. Nakauchi; personal communication), the CD8α-expressing splenocytes in RAG-2$^{-/-}$ mice might represent this lineage.

Co-expression of the Thy-1 antigen and the εchain of the IL-2 receptor is characteristic of cells that represent very immature stages of T cell development. While this population comprises a small proportion (4%) of control thymus, it makes up a major fraction (40%) of the remaining cells in the thymuses of RAG-2$^{-/-}$(FIG. 4C). However, the absence of the CD4 or CD8 single and double positive cell populations results in a dramatic decrease in the cellularity of the thymuses of the mutant mice. Thus, as for immature B cells in the bone marrow, the absolute numbers of immature (Thy-1$^+$/IL-2Rα$^+$) thymocytes only differ by several fold between homozygous mutant and normal mice (data not shown). The above findings indicate that, as seen in B cell development, the majority of developing thymocytes are arrested at an early precursor stage of differentiation. By analogy to the B cell results, it also seems possible that the Thy-1$^+$/IL-2Rα$^+$ population may be analogous to fraction B pro-B cells and represent the T cell differentiation stage immediately prior to TCR rearrangement.

Analysis of TCR and Ig gene rearrangement

To assay for rearrangements of the Ig J$_H$ locus, we used a very sensitive PCR assay (Schlissel, et al., 1991)(FIG. 6). DNA was prepared from bone marrow cells of one month old control mice or RAG-2$^{-/-}$ mice and amplified by a PCR using degenerate Ig heavy chain D and J$_H$3 or J$_H$4 oligonucleotides primers (Schlissel, et al., 1991) to detect DJ$_H$ rearrangements. Hybridization to a J$_H$2J$_H$3-specific probe readily identified DJ$_H$1, DJ$_H$2 and DJ$_H$3 rearrangements on Southern blotted, amplified DNA from control bone marrow cells. However, no rearrangements were detected with 11 separate RAG-2$^{-/-}$ bone marrow DNA preparations. Based on dilution of control samples, we could have detected DJ$_H$ rearrangements in the homozygous mutant DNA if they occurred at a 0.05% the level detected in normal bone marrow cells. In contrast to the RAG-2$^{-/-}$ mice, DJ$_H$ rearrangements were readily detectable in bone marrow DNA from mice homozygous for the scid mutation, indicating that the RAG-2 defect blocks B cell differentiation at an earlier stage than does the scid defect and/or the RAG-2 defect is less leaky.

Figure 7A:
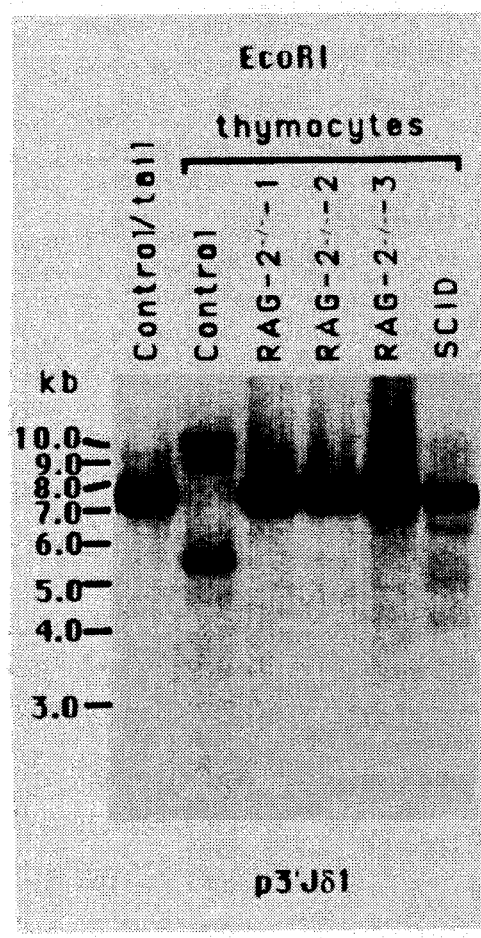
Figure 7B:
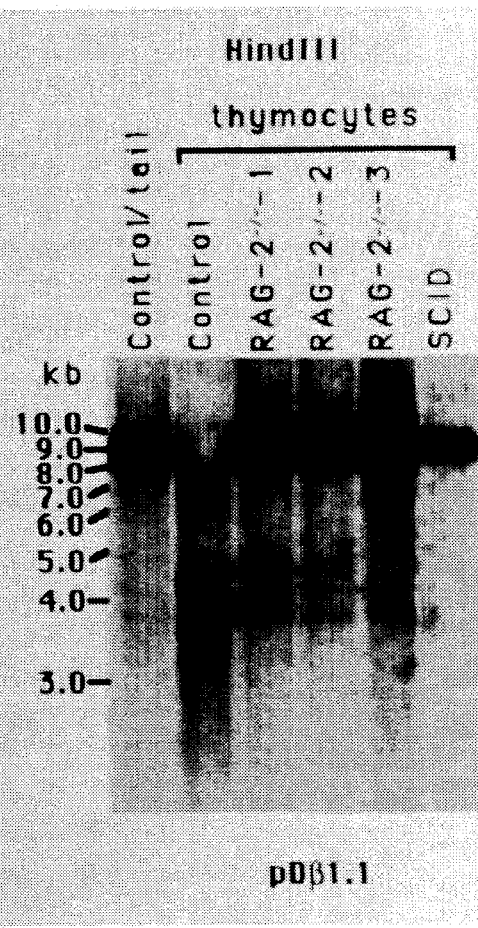

We assayed for rearrangements of the TCRδ (the first TCR locus to rearrange) TCRγ and TCRβ loci in DNA isolated from thymocytes of homozygous mutants and control littermates plus, for direct comparison, thymocytes from scid mice. Genomic DNA was digested with EcoRI or HindIII and assayed by Southern blotting for hybridization to probes that represent sequences 3' to Jδ1 (p3'Jδ1), Jv(p3'Jv1) and Dβ1 (pDβ1.1) and which detect rearrangements of these respective loci. These analyses demonstrated complete rearrangement of the TCRδ locus in thymocytes of control animals and complete lack of detectable rearrangement of this locus in those of RAG-2$^{-/-}$ animals (FIG. 7; left panel). In contrast, as previously observed by others (Carrol and Bosma, 1991), DNA from scid thymocytes showed significant levels of a restricted set of rearrangements of the δ locus (FIG. 7; left panel). These results suggest that, as for B cells, the loss of RAG-2 function results in an earlier and/or more complete block of T cell differentiation than does the scid defect. Finally, hybridization with pJγ1 or pDβ1.1 showed substantial rearrangement of the Jγ locus and nearly complete rearrangement of the TCRβ locus in control thymocytes and complete lack of rearrangement of these loci in the RAG-2 homozygous mutant or scid thymocytes (data not shown; FIG. 7, right panel).

Figure 8:
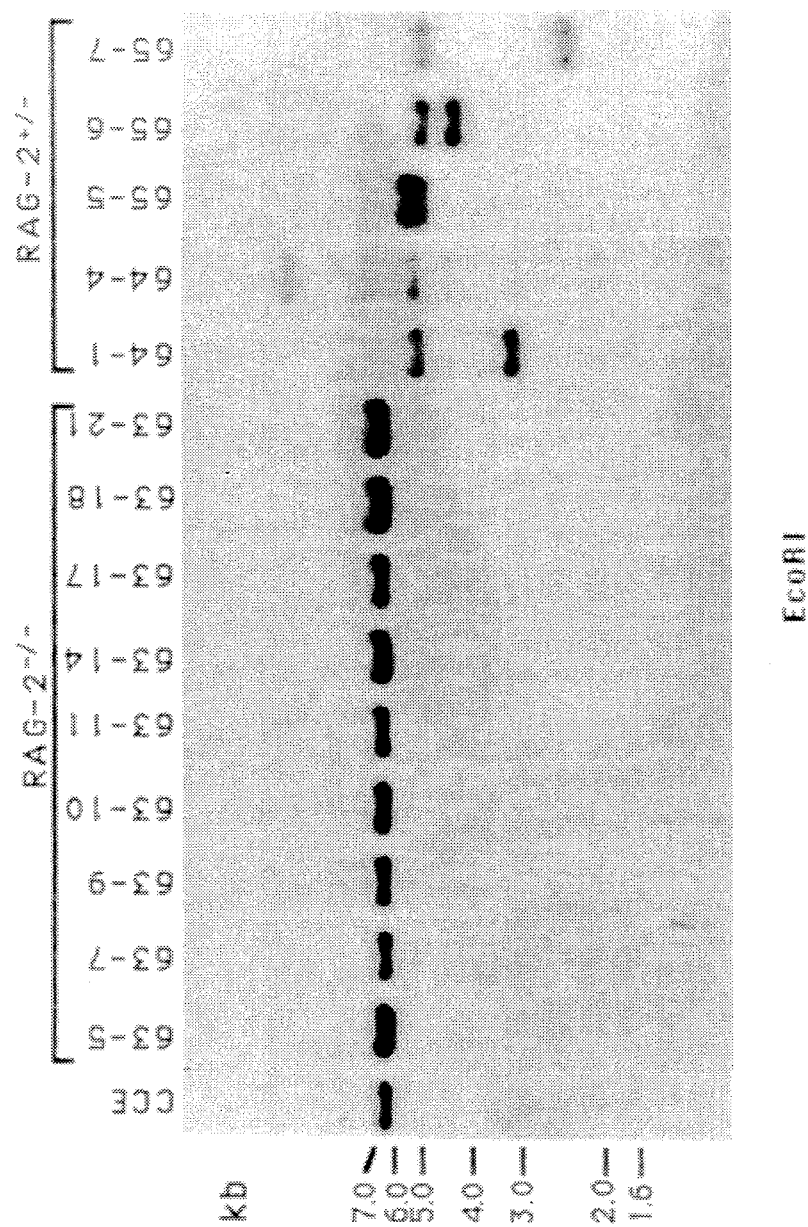

Germ-line Configuration of Ig Genes in A-MuLV-Transformed Fetal Liver Cells of the RAG-2 Mutant Mice The lack of detectable Ig or TCR gene rearrangements in bone marrow and thymuses of RAG-2$^{-/-}$ mice could either be due to the inability to make rearrangements of these loci or to the absence of cells capable of showing such rearrangements. The Abelson murine leukemia virus (A-MuLV) transforms early B lineage cells from the bone marrow and fetal liver; such cells from normal mice usually represent the pre-B stage of differentiation; they have rearranged both J$_H$ loci and express VDJ recombination activity (reviewed by Alt et al., 1986). The A-MuLV transformation efficiency was not significantly different between RAG-2$^{-/-}$ and RAG-2$^{+/-}$ mice demonstrating that the RAG-2 mutation did not block B cell differentiation at a stage prior to susceptibility to this virus; similar conclusions were previously reached with respect to the scid defect (Schuler et al., 1986; Fulop et al., 1988). We established 25 RAG-2$^{-/-}$ A-MuLV transformed cell lines and 10 lines from RAG-2$^{+/-}$ counterparts. Genomic DNA from these lines was digested with EcoRI and assayed for rearrangements of the J$_H$ locus by hybridization to a specific probe (FIG. 8). As expected, DNA from the control lines showed no detectable germline fragment and two or more rearranged J$_H$ hybridizing fragments representing rearrangements of both J$_H$ loci. In contrast, the J$_H$ locus was in germ-line configuration in DNA from the homozygous mutant cell lines with no detectable rearrangements (FIG. 8). Furthermore, no D to J rearrangements were detectable in DNA from the homozygous mutant lines by the sensitive PCR assay, confirming the complete lack of VDJ recombination activity at this locus in these lines (data not shown).

To further characterize the phenotype of the A-MuLV transformants from the homozygous RAG-2 mutant mice, we assayed RNA from these lines for expression of a series of pre-B specific genes. The λ5 and germline Ig V$_H$ genes are expressed specifically in precursor B cells (Sakaguchi and Melchers, 1986; Yancopoulos and Alt, 1985), the interleukin-7 receptor and terminal deoxynucleotidyl transferase genes are expressed specifically at the precursor stage within the B cell lineage (Park et al., 1990; reviewed by Silverstone et al., 1978), and the germline Ig Cμ gene is thought to be transcribed in developing B lineage cells in conjunction with its activation as a target for VDJ rearrangement (Lenon and Perry, 1986). We detected similar expression levels of all of these transcripts in homozygous mutant and heterozygous control cells (FIG. 9 and data not shown).

Figure 9:
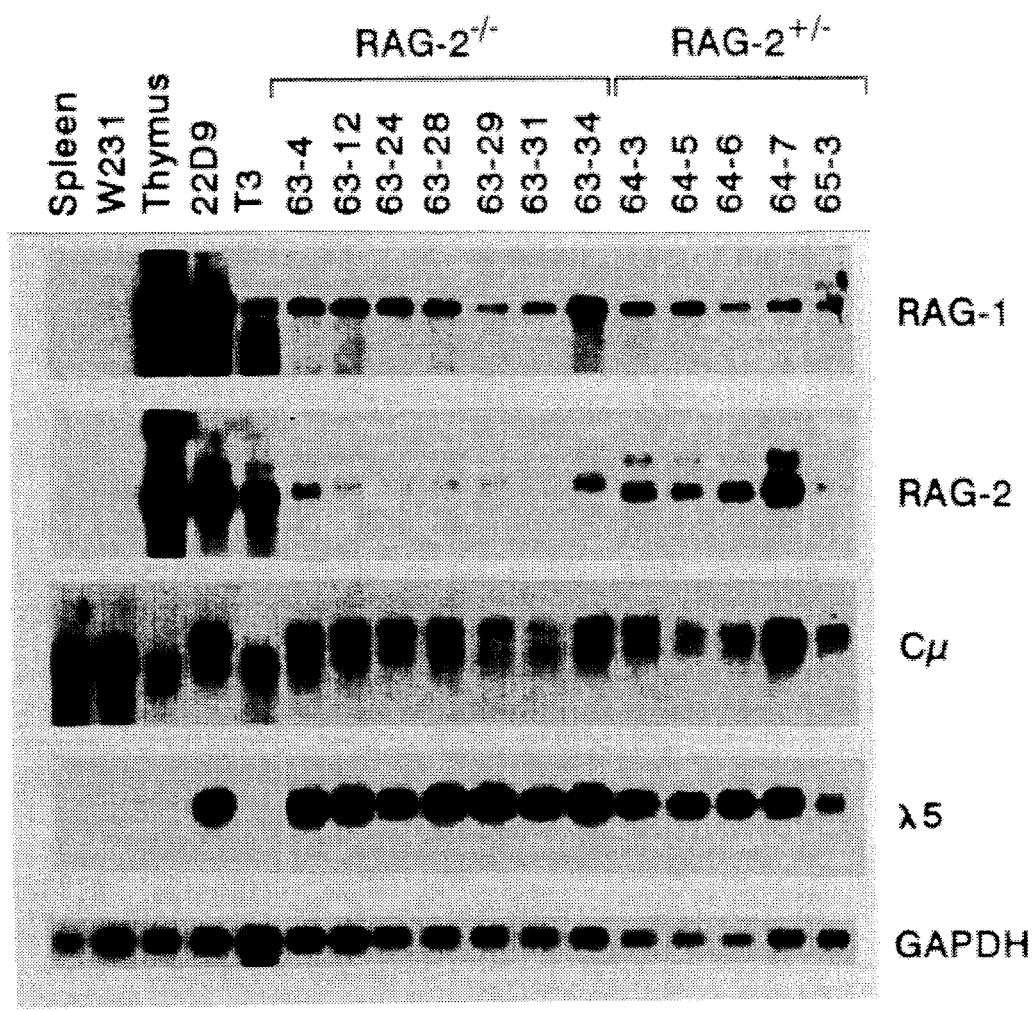

Expression of transcripts from the RAG-1 and RAG-2 genes also was detected in all of the homozygous mutant and heterozygous control A-MuLV transformants with no consistent differences between mutant and control lines (FIG. 9). The RAG-2 transcripts in the RAG-2$^{-/-}$ lines were, as expected, larger than normal RAG-2 transcripts due to the replacement of the RAG-2 coding sequences with the PMCl-NeopA$^+$ gene fragment; we confirmed this interpretation by showing that the mutant RAG-2 transcript hybridized to a PMClneo probe (data not shown). Finally, the mutant RAG-2 transcript is expected to hybridize less intensely than the normal transcript due to the fact that it lacks a significant portion of the sequences contained in the RAG-2 probe used in the assay. Therefore, the relative levels of these two transcripts in heterozygous lines are not as divergent as their relative hybridization intensities (FIG. 9).

We conclude that A-MuLV transformants derived from the RAG-2$^{-/-}$ animals appear identical to their RAG-2$^{+/-}$ counterparts except for the expression of the mutant RAG-2 RNA and the lack of detectable J$_H$ rearrangements. Together, the analyses of A-MuLV transformants from homozygous RAG-2 mutants indicate that the RAG-2 deficiency blocks B cell development at a point corresponding to the onset of VDJ recombination. The results further support the notion that the defect in B cell development may result solely from inability to initiate VDJ recombination as opposed to some more general defect in the regulation of gene expression.

Complementation of the RAG-2 Defect

Ability to complement the RAG-2 mutation in cell lines and mice should offer a powerful system for studies aimed at dissecting the function of this gene and elucidating the initial events in the Ig gene rearrangement process. The RAG gene locus is a complex of (at least) two closely linked genes of which both have been implicated as required for VDJ recombination in non-lymphoid cells. Integration of transfected DNA can be associated with deletions or insertions beyond the integration site, raising the possibility that the observed phenotype of RAG-2$^{-/-}$ mice might result from genetic alterations in flanking DNA sequences such as the RAG-1 gene. To confirm that the lack of RAG-2 function was the only defect in RAG-2$^{-/-}$ cells and determine whether this defect could be complemented, we asked whether introduction of a RAG-2 expression vector into homozygous mutant A-MuLV transformants could restore their ability to undergo VDJ recombination. For this purpose we used a transient VDJ recombination assay in which substrates are first introduced into mammalian cells and then recovered and assayed in bacteria for those that have undergone VDJ recombination (Hesse et al., 1987).

The transient VDJ recombination substrate was introduced into RAG-2$^{-/-}$ mutant or RAG-2$^{+/-}$ control A-MuLV transformants either alone or in combination with RAG-1 or RAG-2 expression vectors driven by an Ig heavy chain V$_H$ promoter and Eμ enhancer element. No VDJ recombination activity was detected in homozygous mutant cell lines in the absence of co-transfected RAG expression vectors or with the co-transfected RAG-1 expression vector (Lines 63-12 and 63-31; Table 1 below). However, co-transformation with the RAG-2 expression vector resulted in the appearance of substantial levels of VDJ recombination activity (Table 1). The level of VDJ recombination activity measured by this semiquantitative assay (Lieber et al., 1987) in homozygous mutant lines co-transfected with RAG-2 was similar to that observed in the control line (Line 64-3) assayed alone or with co-transfected expression constructs (Table 1). Simultaneous introduction of the same RAG-1 and RAG-2 expression constructs into normal lymphoid cell lines that lack VDJ recombination activity conferred this activity whereas introduction of either one alone did not (data not shown). Therefore, lack of RAG-2 function is the sole defect that leads to lack of VDJ recombination activity in the RAG-2$^{-/-}$ A-MuLV transformed cells.

TABLE 1

TRANSIENT RECONSTITUTION OF VDJ RECOMBINATIONAL ACTIVITY BY RAG-2 TRANSFECTION INTO RAG-2$^{-/-}$ A-MULV TRANSFORMANTS

| Cell Line | DNA$ | Amp$^R$ | Amp$^R$Cam$^R$ | R* |
|---|---|---|---|---|
| 63-12 | — | 10,600 | 0 | 0 |
| (RAG-2$^{-/-}$) | PDRI | 1,640 | 0 | 0 |
| | PDRII | 340 | 8 | 2.4 |
| 63-31 | — | 27,000 | 10# | 0.04 |
| (RAG-2$^{-/-}$) | PDRI | 8,750 | 0 | 0 |
| | PDRII | 1,750 | 45 | 2.6 |
| 64-3 | — | 7,600 | 373 | 4.9 |
| (RAG-2$^{+/-}$) | PDRI | 1,220 | 95 | 7.8 |
| | PDRII | 300 | 12 | 4.0 |

$ Each cell line was transfected with a recombination substrate pJH200 only (−) or / pJH200 plus the RAG-1 (PDRI) or RAG-2 (PDRII) expression vectors driven by JH promotor and a IgH enhancer.
* The percentage of recombination, R, is calculated as the percentage of Amp$^R$Cam$^R$ colonies/Amp$^R$ colonies.
Colonies of Amp$^R$/Cam$^R$ were randomly picked, and pJH200 was analyzed for appropriate rearrangements by HindIII digestion. pJH200 isolated from these 10 colonies did not show any rearrangements.

Lack of RAG-2 Activity Affects Only Lymphocytes

As mentioned above, homozygous RAG-2 mutant mice appeared normal except for the immunological defects. To examine the animals for other possible manifestations of this mutation, we performed a microscopic pathological analysis of various tissues from heterozygous and homozygous mutant 4–5 wk old mice. As described above, spleens, thymuses, and lymph nodes of homozygous mutant animals were all small and hypoplastic. In contrast, no detectable alterations were observed in a variety of other tested tissues including liver, kidney, pancreas, brain, heart, lung, intestine, and gonads. Of particular note, histochemical analyses revealed no recognizable differences in the brains of adult control and homozygous mutant animals; in this context, we also observed no obvious behavioral differences between mutant and control animals that were unrelated to their immunological defects. Furthermore, both male and female RAG-2$^{-/-}$ animals were fertile.

We also assayed for the presence of several non-lymphoid cell types that have been suggested to potentially express VDJ recombinase activity during their development. It has been proposed that VDJ recombinase activity may be involved in the generation of receptors on NK cells. NK cells are present in SCID mice (Dorshkind et al., 1985); however, because the scid defect does not involve the specific components of the VDJ recombinase system, one cannot unequivocally rule out a role for this activity in their development. To directly test this possibility, we employed the YAC-1 target cell lysis system to assay for NK cell activity of control and RAG-2$^{-/-}$ splenocytes. In two separate experiments, the homozygous mutant mice had a greater level of splenic NK activity than found in control littermates (Table 2). The increased numbers of these cells types may reflect, at least in part, expansion of this population to fill the void left by the lack of a mature lymphocyte population.

TABLE 2

NK ACTIVITY OF MICE HOMOZYGOUS FOR THE RAG-2 MUTATION

| Expt. | Effector | Cells[a] | % Lysis of YAC-1 at E:T Ratios of | | |
|---|---|---|---|---|---|
| | | | 20:1 | 50:1 | 100:1 |
| 1 | Control | spleen | 3.6 | 7.9 | 12.1 |
| | Control | spleen | 4.7 | 9.0 | 13.4 |
| | RAG-2-/--1 | spleen | 10.5 | 16.8 | 27.6 |
| 2 | Control | spleen | 6.4 | 8.8 | 8.0 |
| | RAG-2-/--2 | spleen | 8.2 | 10.4 | 13.5 |
| | RAG-2-/--3 | spleen | 26.2 | 39.4 | 48.5 |

[a]spleen cells were harvested after 24 h poly IC stimulation in vivo (100 μg/mouse).

Certain tumors of the myeloid/monocyte lineage have been found to have $DJ_H$ rearrangements and other tumors have been found to have potential to differentiate into either the monocyte or B lymphoid lineages (Klinken et al., 1988). Based on FACS analysis for expression of macrophage-specific (Mac-1) or granulocyte-specific (8C5) markers, we found that spleens of homozygous mutant mice also contained increased numbers of macrophages and granulocytes compared to wild-type littermates (FIG. 5F and data not shown) suggesting that the lack of RAG-2 function and VDJ recombination activity does not affect development of these cell types.

Experimental Discussion

The Homozvaous RAG-2 Mutation Results in Lack of Ability to Initiate VDJ Recombination Mice homozygous for a mutation that disrupts the RAG-2 gene lack mature B and T cells. The defect in these mice appears to be total inability to initiate the VDJ rearrangement process. Thus, these animals contain normal or even increased numbers of very immature B and T cells that represent the stage in which VDJ recombination is initiated. This phenotype is consistent with a role for the RAG-2 gene product as an essential component of th VDJ recombinase system. In this context, the expression pattern of pre-B specific genes (including RAG-1) is apparently normal in A-MuLV transformants from RAG-2$^{-/-}$ animals suggesting that the RAG-2 gene product is not involved in regulating expression of genes specific to this cell type. The specificity of the RAG-2 defect is further demonstrated by our ability to complement the mutation and restore VDJ recombination activity to homozygous mutant A-MuLV transformed pre-B cells via introduction of a function RAG-2 expression vector. The ability of the RAG-1 and RAG-2 gene to synergistically confer VDJ recombination activity to non-lymphoid cells strongly indicated a physiological role for these genes in the normal VDJ recombination process (Oettinger et al., 1990). Our studies provide direct physiological proof that RAG-2 gene function is necessary for lymphocyte-specific VDJ recombination in normal developing lymphocytes. In addition, our findings also support the notion that continued development of lymphocytes is linked to their ability to rearrange and express antigen receptor loci.

The RAG-2 Mutation Affects an Earlier Stage of VDJ Recombination than the Scid Mutation The primary manifestation of the murine scid mutation is the lack of mature B or T lymphocytes due to an impairment in the VDJ joining process. However, unlike the RAG-2 mutation, the scid mutation does not affect the lymphocyte specific components of the VDJ recombinase system, but rather affects an more generalized activity involved in DNA repair (Fulop and Phillips, 1990; Biedermann et al., 1991; hendrickson et al., 1991) and also involved in the final VDJ recombination step in which free coding segment ends are joined (Malynn et al., 1988; Lieber et al., 1988; Blackwell et al., 1989). Thus, although the general phenotype of RAG-2$^{-/-}$ mice is in many ways similar to that of mice homozygous for the scid mutation, there are several notable differences (Table 3). Consistent with the fact that the scid mutation does not affect the initiation of the VDJ recombination process, rearrangements of the Ig $J_H$ and TCR Jδ locus are readily detectable in primary lymphoid organs of scid mutated mice (Carroll and Bosma, 1991; FIG. 3). Likewise, A-MuLV transformants from scid mutated mice generally have rearranged both $J_H$ loci (Schuler et al., 1986) and continue to rearrange this locus during growth in culture (Malynn et al., 1988). In contrast, no rearrangements of any antigen receptor locus are detectable in primary lymphoid organs from mice homozygous for the RAG-2 mutation and A-MuLV transformants from these mice have no detectable rearrangements of the $J_H$ locus.

TABLE 3

PHENOTYPIC COMPARISON OF RAG-2 DEFICIENT AND SCID MICE

| | RAG-2-/- | C.B-17[scid/scid] |
|---|---|---|
| thymus | Rudimentary | rudimentary |
| serum IgM level | negative | negative |
| B lineage cell population | no sIgs+ cells some CD45R (B220)+/ CD43+ cells | no sIgs+ cells some CD45R (B220)+/ CD43+ cells |
| D-J rearrangements (PCR assay) | undetectable | detectable |
| A-MuLV-transformed cell lines | | |
| Igh gene locus | germ-line | abnormal D-J rearrangements |
| Expression of | | |
| RAG-1 | + | + |
| RAG-2 | + (mutated) | + |
| λ5 | + | + |
| germ-line μ | + | + |
| VHJ558 | + | + |
| IL-7R | + | + |
| TdT | + | + |
| T lineage cell population | no TCR+/CD3+ cells no CD4+/ CD8+ thymocytes | no TCR+/CD3+ cells no CD4+/ CD8+ thymocytes |
| TCR gene rearrangements | | |
| TCRα | N D* | germ-line |
| TCRβ | germ-line | germ-line |
| TCRγ | germ-line | germ-line |
| TCRδ | germ-line | Dδ1-Jδ1, Dδ2-Jδ1 |
| NK cell population | intact | intact |

*not done

The scid mutation has been shown to be "leaky" at a significant level. Various lines of evidence have suggested that this leakiness in many cases may be explained by the ability of the Scid VDJ recombination process to occasionally form functional VDJ joins (Ferrier et al., 1989; Hendrickson et al., 1990; Petrini et al., 1990). To date, we have not observed any leakiness of the homozygous RAG-2 mutation, although this issue is under continued examination. A relative lack of leakiness of the RAG-2 mutation compared to the scid mutation would be consistent with the fact that the former mutation completely obviates VDJ recombination while the latter does not. The scid mice have proven to be a remarkable model for many different types of studies including allogeneic transplantation studies. The RAG-2 mutant mice may serve this purpose even better, both because their defect is limited solely to the VDJ recombination process and also because they may prove to be much less leaky.

Most characterized human mutations that lead to a severe combined immune deficient phenotype affect enzymatic activities (such as adenosine deaminase) that are not involved with the VDJ recombination system and none have been described that clearly involve RAG gene function (review by Geha et al., 1992). A possible explanation for the absence of characterized human SCID phenotypes that involve RAG genes would be that loss of RAG function has embryonic lethal consequences. However, our murine studies clearly suggest individuals carrying mutations that debilitated RAG-2 gene function would be expected to occur as the RAG-2 gene product does not seem to be obligatory for any function outside of the immune system. More thorough characterization of certain human patients that do not fall into the more common SCID patterns may reveal RAG gene impairments.

The RAG-2 mutation appears to affect only the immune system

Low level expression of RAG genes in tissues outside of the immune system has led to speculation that RAG gene products may participate in the development of cells and organs in addition to lymphocytes (reviewed by Altet al., 1991). We have observed absolutely no evidence for any manifestation of the RAG-2 mutation other than the block in T and B lymphocyte development. We conclude that neither an unknown activity conferred by RAG-2 alone nor VDJ recombinase activity is required for the development of cells other than lymphocytes.

The finding of low level RAG-1 expression in murine brain has been interpreted to imply a role for the product of that gene in the development or maintenance of the nervous system (Chun et al., 1991). In this context, a recent report further concluded that some cells in the brain are capable of specifically rearranging transgenic VDJ recombination substrates (Matsuoka et al., 1991). Clearly, classical VDJ recombinase activity is not essential for the apparently normal development of tissues of the central nervous system including the brain as evidenced by the normal development of these tissues in RAG-2 mutant animals. In addition, we do not detect rearrangements either of endogenous Ig genes (even by sensitive PCR assays) or of introduced recombination substrates in either normal or A-MuLV transformed homozygous RAG-2 mutant precursor lymphocytes; even though such cells clearly produce functioning RAG-1 gene products. Therefore, as suggested by transfection studies in non-lymphoid cells (Oettinger et al., 1990), expression of the endogenous RAG-1 gene product in lymphoid cells confers no VDJ recombinase activity. These findings indicate putative VDJ-like recombination events in the brain are unlikely to be mediated by RAG-1 activity alone. However, it remains possible that such rearrangements could be mediated by RAG-1 in conjunction with a brain specific co-factor or by a totally novel system that allows recognition of the VDJ RS sequences.

Our findings do not eliminate potential roles for VDJ recombinase or the RAG-2 gene product in certain other types of lymphocyte-specific or more generalized processes. The apparent high-level expression of only RAG-2 in the chicken bursa has been interpreted to imply a role for the product of that gene in the site-specific Ig gene conversion process (Carlson etal., 1991). In this regard, it is conceivable that the RAG-2 gene product (or RAG-1 gene product) could have a role in other mammalian B cell-specific functions such as Ig heavy chain class switching or somatic mutation. The availability of homozygous RAG-2 mutant mice should allow such ideas to be tested through approaches that involve complementation of the defect with rearranged Ig transgenes designed to assay for such processes. In addition, the possibility remains open that the RAG-2 gene product may carry out a totally unexpected function that is unrelated to site-specific VDJ recombination and not involved in normal development, such as the speculative role of RAG-1 in suppression of recombination in long-lived cells (Chun et al., 1991). Longer term observation of animals and more strict tests of behavior and relative fertility will be necessary to unequivocally address this possibility.

REFERENCES

1. Akira, S., Okazaki, K., and Sakano, H. (1987). Two pairs of recombination signals are sufficient to cause immunoglobulin V-(D)-J joining. Science 238:1134–1138.
2. Alt, F. W., Blackwell, T. K., DePinho, R. A., Reth, M. G., and Yancopoulos, G. D. (1986). Regulation of genome rearrangement events during lymphocyte differentiation. Immuno 1. Rev. 89:5–30.
3. Alt, F. W., Rathbun, G., and Yancopoulos, G. D. (1991) Gene Rearrangement in the Brain. Current Biology, 1:3–5.
4. Biedermann, K. A., Sun, J., Giaccia, A. J., Tosto, L. A., and Brown M. (1991). Scid mutation in mice confers hypersensitivity to ionizing radiation and a deficiency in DNA double-strand break repair. Proc. Natl. Acad. Sci. USA 88:1394–1397.
5. Blackwell, T. K., Moore, M. W., Yancopoulos, G. D., Suh, H., Lutzker, S., Selsing, R., and Alt, F. W. (1986). Recombination between immunoglobulin variable region segments is enhanced by transcription. Nature 324:585–589.
6. Blackwell, T. K., Malynn, B. A., Pollock, R. R., Ferrier, P., Covey, L., Fulop, G. M., Phillips, R. A., Yancopoulos, G. D., and Alt, F. W. (1989). Isolation of scid pre-B cells that rearrange kappa light chain genes: formation of normal signal and abnormal coding joins. EMBO J. 8:735–642.
7. Blackwell, T. K., and Alt, F. W. (1989). Molecular characterization of the lymphoid V(D)J recombination activity. J. Biol. Chem. 264: 10327–10330.
8. Bosma, G. C., Fried, M., Custer, R. P., Carroll, A. M., Gibson, D. M., Bosma, M. J. (1988). Evidence of functional lymphocytes in some (leaky) SCID mice. J. Exp. Med. 167:1016–1033.
9. Bosma, M. J., and Carroll, A. M. (1991). The Scid mouse mutant: definition, characterization, and potential uses. Annu. Rev. Immunol. 2:323–350.
10. Bothwell, A. L. M., Paskind, M., Reth, M., Imanishi-Kari, T., Rajewsky, K., and Baltimore, D. (1981). Heavy chain variable region contribution to the NP$^b$ family of anitbodies: somatic mutation evident in a γ2a variable region. Cell 24:625–637.
11. Carlson, L. M., Oettinger, M. A., Schatz, D. G., Masteller, E. L., Hurley, E. A., McCormack, W. T., Baotimore, D., and Thompson, C. B. (1991). Selective expression of RAG-2 in chicken B cells undergoing immunoglobulin gene conversion. Cell 64:201–208.

12. Carroll, A. M., and Bosma, M. J. (1991). T-lymphocyte development in Scid mice is arrested shortly after the initiation of T-cell receptor d gene recombination. Genes Dev. 5:1357–1366.

13. Carroll, A. M., and Bosma, M. J. (1988). Detection and characterization of functional T cells in mice with severe combined immune deficiency. Eur. J. Immunnol. 18:1965–1971.

14. Carroll, A. M., Hardy, R. R., Bosma, M. J. (1989). Occurrence of mature B ( IgM$^+$ B220$^+$) and T ( CD3$^+$) lymphocytes in SCID mice. J. Immunol. 143:1087–1093.

15. Cesano, A., O'Connor, R., Lange, B., Finan, J., Royera, G., and Santoll, D. (1991). Homing and progression patterns of childhood acute lymphoblastic leukemias in severe combined immunodeficiency mice. Blood 77:2463–2474.

16. Chien, Y., Iwashima, M., Wettstein, D. A., Kaplan, K. B., Elliott, J. F., Born, W., and Davis, M. M. (1987). T-cell receptor d gene rearrangements in early thymocytes. Nature 330:722–727.

17. Chun, J. J., Schatz, D. G., Ottenger, M. A., Jaenisch, R., and Baltimore, D. (1991). The recombination activating gene-1 (RAG-1) transcript is present in the murine central nervous system. Cell 64:189–200.

18. DeLord, C. Clutterbuch, R., Titley, J., Ormerod, M., Gordon-Smith, T., Millar, J., and Powles, R. (1991). Growth of primary human acute leukemia in severe combined immunodeficient mice. Exp. Hematol. 19:991–993.

19. Dorshkind, K., Denis, K. A., and Witte, O. N. (1986). Lymphoid bone marrow cultures can reconstitute heterogeneous B and T cell-dependent responses in severe combined immunodeficient mice. J. Immunol. 137:3457–3463.

20. Dorshkind, K., Pollack, S. B., Bosma, M. J., and Phillips, R. A. (1985). Natural killer (NK) cells are present in mice with severe combined immunodeficiency (scid). J. Immunol. 134:3798–3801.

21. Dorshkind, K., Yoshida, S., and Gershwin, M. E. (1989) Bone marrow cells from young and old New Zealand black mice can reconstitute B lymphocytes in severe combined immunodeficient recipients. J. Autoimmun. 2:173–186.

22. Ferrier, P., Covey, L. R., Li, S. C., Suh, H., Malynn, B. A., Blackwell, K., Moureen, A. M., and Alt, F. W. (1990). Normal recombination substrate $V_H$ to $DJ_H$ rearrangements in pre-B cell lines from Scid mice. J. Exp. Med. 171:1909–1918.

23. Finkel, T. H. Kubo, R. T., and Cambier, J. C. (1991) T-Cell development and transmembrane signalling: changing biological responses through an unchanging receptor. Immunology Today 12:79–85.

24. Fort, P. L., Marty, L., Piechaczyk, M., ElSabrouty, S., Dani, C., Jeanteur, P., and Blanchard, J. M. (1985). Various rat adult tissues express only one major mRNA species from the glyceraldehyde-3-phosphate-dehydrogenase multigene family. Nucleic Acids Res. 13:1431–1442.

25. Fulop, G. M., Bosma, G. C., Bosma, M. J., and Phillips, R. A. (1988). Early B-cell precursors in scid mice: normal numbers of cells transformable with abelson murine leukemia virus (A-MuLV). Cell. Immunol. 113:192–201.

26. Fulop, G. M., and Phillips, R. A. (1990). The scid mutation in mice causes a general defect in DNA repair. Nature 347:479–482.

27. Fulop, G. M., Wu, D. -D., and Phillips, R. A. (1989). The SCID mouse as a model to identify and quantify myeloid and lymphoid stem cells. Curr. Top. Microbiol. Immunol. 152:173–179.

28. Geha, R. S., Rosen, F. S., and Chaatila, T. (1992) Primary immunodeficiency diseases In: Hematology of Infancy and Childhood W. B. Saunders Co.

29. Hardy, R. R., Kemp, J. D., and Hayakawa, K. (1989). Analysis of lymphoid populations in scid mice: detection of a potential B lymphocyte progenitor population present at normal levels in Scid mice by three color flow cytometry with B220 and S7. Cur. Topics in Mircobiol. and Immunol. 152:19–25.

30. Hardy, R. R., Carmack, C. E., Shinton, S. A., Kemp, J. D., and Hayakawa, K. (1991). Resolution and characterization of pro-B and pre-pro-B cell stages in normal mouse bone marrow. J. Exp. Med. 173:1213–1225.

31. Hendrickson, E. A., Schlissel, M. S., and Weaver, D. T. (1990). Wild-type V(D)J recombination in scid pre-B cells. Mol. Cell. Biol. 10:5397–5407.

32. Hendrickson, E. A., Qin, S., Bump, E. A., Schatz, D. G., Oettinger, M., and Weaver, D. T. (1991). A link between double-strand break-related repair and V(D)J recombination: the scid mutation. Proc. Natl. Acad. Sci. USA 88:4061–4065.

33. Hesse, J. E., Lieber, M. R., Gellert, M., and Mizuuchi, K. (1987). Extrachromosomal DNA substrates in pre-B cells undergo inversion or deletion as immunoglobulin V-(D)-J joining signals. Cell 49:775–783.

34. Hesse, J. E., Liber, M. R., Mizzuchi, K., and Gellert, M. (1989). V(D)J recombination: a functional definition of the joining signals. Gene Dev. 3:1053–1061.

35. Kaneshima, H., Shih, C. C., Namikawa, R., Rabin, L., Outzen, H., Machado, S. G., McCune, J. M. (1991). Human immunodeficiency virus infection of human lymph nodes in the SCID-hu mouse. Proc. Natl. Acad. Sci. 88:4523–4527.

36. Klinken, P. S., Alexander, W. S., and Adams, J. (1988) Hemopoietic lineage switch: v-raf oncogene converts Eμmyc transgenic B-cells into macrophages. Cell 53:857–867.

37. Lenon, G., and Perry, R. P. (1986) Cμ-containing transcripts initiate heterogeneously within the IgH enhancer region and contain a novel 5' nontranslatable exon. Nature 318:475–477.

38. Lewis, S., and Gellert, M. (1989). The mechanism of antigen receptor gene assembly. Cell 59:585–588.

39. Lieber, M. R., Hesse, J. E., Mizuuchi, K., and Gellert, M. (1987). Developmental stage specificity of the lymphoid V(D)J recombination activity. Genes Dev. 1:751–761.

40. Lieber, M. R., Hesse, J. E., Lewis, S., Bosma, G. C., Rosenberg, N., Mizuuchi, K., Bosma, M. J., and Gellert, M. (1988). The defect in murine severe combined immune deficiency: joining of signal sequences but not coding segment in V(D)J recombination. Cell 55:7–16.

41. London, N. J., Thirdborough, S. M., Swift, S. M., Bell, P. R. and James, R. F. (1991). The diabetic "human reconstituted" severe combined immunodeficient (SCID-hu) mouse: a model for isogeneic, allogeneic, and xenogeneic human islet transplantation. Transplant Proc. 23:749.

42. Malynn, B. A., Blackwell, T. K., Fulop, G. M., Rathbum, G. A., Furley, A. J. W., Ferrier, P., Heinke, L. B., Phillips, R. A., Yancopoulos, G. D., and Alt, F. W. (1988). The Scid defect affects the final step of the immunoglobulin VDJ recombinase mechanism. Cell 54:453–460.

43. Mansour, S. L., Thomas, K. R., and Capecchi, M. R. (1988). Disruption of the proto-oncogene int-2 in mouse embryo-derived stem cells: a general strategy for targeting mutations to non-selectable genes. Nature 36:348–352.

44. Matsuoka, M., Nagawa, F., Okazaki, K., Kingsbury, L., Yoshida, K., Muller, U., Larue, D. T., Winer, J. A., and Sakano, H. (1991). Detection of somatic DNA recombination in the transgenic mouse brain. Science 254:81–86.
45. McCune, J. M. (1991). SCID mice as immune system models. Curr. Opin. Immunol. 3:224–228.
46. McCune, J. M., Kaneshima, H., Lieberman, M., Weissman, I. L., and Namikawa, R. (1989) The SCID-hu mouse: current status and potential applications. Curr. Top. Microbiol. Immunol. 152:183–193.
47. Mosier, D. E. (1990). Immunodeficient mice xenografted with human lymphoid cells: new models for in vivo studies of human immunobiology and infectious disease. J. Clinical Immunology 10:185–191.
48. Murphy, W. J. Kumar, V., and Bennett, M. (1989). Immunobiology of bone marrow transplantation: Studies using SICD mice: Curr. Top. Microbiol. Immunol. 152:251–258.
49. Nomura, T., Takahama, Y., Hongyo, T., Takatera, H., Inohara, H., Fukushima, H., Ono, S., and Hamaoka, T. (1991) Rapid growth and spontaneous metastasis of human germinal tumors ectopically transplanted into SCID (severe combined immunodeficiency) and SCID-nude streaker mice. Jpn. J. Cancer Res. 82:701–709.
50. Nomura, T., Takahama, Y., Hongyo, T., Inohara, H., Takatera, H., Fukushima, H., Ishii, Y., and Hamaoka, T. (1991). SCID (severe combined immunodeficiency) mice as a new system to investigate metastasis of human tumors. J. Radiat. Res. 31:288–292.
51. Oettinger, M. A., Schatz, D. G., Gorka, C., and Baltimor, D. (1990). RAG-1 and RAG-2, adjacent genes that synergistically activate V(D)J recombination. Science 248:1517–1523.
52. Park, L. S., Freind, D. J., Schmeire, A. E., Dower, S. K., and Namen, A. E. (1990). Murine interleukin-7 (IL-7) receptor. J. Exp. Med. 171:1073–1089.
53. Parks, D. R., Lanier, L. L., and Herzenberg, L. A. (1986). Flow cytometry and fluorescence activated cell sorting (FACS). In handbook of Experimental Immunology, D. M. Weir, L. A. Herzenberg, C. C. Blackwell, and L. A. Herzenberg, eds. (London: Blackwell Scientific), pp. 29.1–29.21.
54. Plillips, R. A., Jewett, M. A. S., and Gallie, B. L. (1989) Growth of human tumors in immune-deficient SCID mice and nude mice. Curr. Top. Microbiol. Immunol. 152:259–263.
55. Rolink A., and Melchers, F. (1991). Molecular and cellular origins of B lymphocyte diversity. Cell 66:1081–1094.
56. Roths, J. B., Marshall, J. D., Allen, R. D., Carlson, G. A. and Sidman, C. L. (1990). Spontaneous Pneumocystis carinii pneumonia in immunodeficient mutant SCID mice: natural history and pathology. Am. J. Pathol. 136:1173–1186.
57. Sakaguchi, N., and Melchers, F. (1986). 15, a new light chain-related locus selectively expressed in pre-B lymphocytes. Nature 324:579–582.
58. Schaible, U. E., Kramer, M. D., Museteanu, C., Zimmer, G., Mossmann, H., and Simon, M. M. (1989). The severe combined immunodeficiency (SCID) mouse: a laboratory model for the analysis of lyme arthritis and carditis. J. Exp. Med. 170:1427–1432.
59. Schatz, D. G., and Baltimore, D. (1988). Stable expression of immunoglobulin gene V(D)J recombinase activity by gene transfer into 3T3 fibroblasts. Cell 53:107–115.
60. Schatz, D. G., Oettinger, M. A., and Baltimore, D. (1989). The V(D)J recombination activating gene, RAG-1. Cell 59:1035–1048.
61. Schlissel, M. S., Corcoran, L. M., and Baltimore, D. (1991). Virus-transformed pre-B cells show ordered activation but not inactivation of immunoglobulin gene rearrangement and transcription. J. Exp. Med. 173:711–720.
62. Scbanidt-Wolf, I. G., Negrin, R. S., Kiem, H. P., Blume, K. G., and Weissman, I. L. (1991). Use of a SCID mouse/human lymphoma model to evaluate cytokine-induced killer cells with potent antitumor cell activity. J. Exp. Med. 174:139–149.
63. Schuler, W., Weiler, I. J., Schuler, A., Phillips, R. a., Rosenberg, N., Mak, T. W., Kearney, J. F., Perry, R. P., and Bosma, J. J. (1986). Rearrangement of antigen receptor genes is defective in mice with severe combined immune deficiency. Cell 46:963–972.
64. Schwartzberg, P. L., Robertson, E. J., and Goff, S. P. (1990). Targeted gene disruption of the endogenous cable locus by homologous recombination with DNA encoding a selectable fusion protein. Proc. Natl. Acad. Sci. USA 87:3210–3214.
65. Silverstone, A. E., Rosenberg, N., Baltimore, D., Sato, V. L., Scheid, M. P., and Boyse, E. A. (1978). Correlating terminal deoxynucleotidyl transferase and cell-surface markers in the pathway of lymphocyte ontogeny. In Differentiation of normal and neoplastic hematopoietic cells (Cold Spring Harbor Laboratory). 433–453.
66. Siu, G., Kronenberg, M., Strauss, E., Haars, R., Mak, T. W., and Hood, L. (1984). The structure, rearrangement and expression of Db gene segments of the murine T-cell antigen receptor. Nature 311:344–350.
67. Yancopoulos, G. D., Alt, F. W. (1985). Developmentally controlled and tissue specific expression of unrearranged VH gene segments. Cell 40:271–281.
68. Yancopoulos, G. D., Blackwell, T. K., Suh, H., Hood, L., and Alt, F. W. (1986). Introduced T cell receptor variable region gene segments recombine in pre-B cells: evidence that B and T cells use a common recombinase. Cell 44:251–259.
69. Yancopoulos, G. D., Oltz, E. M. Rathbun, G., Berman, J. E., Smith, R. K., Lansford, R. D., Rothman, R., Okada, A., Lee, G., Morrow, M., Kaplan, K., Prockop, S., and Alt, F. W. (1990). Isolation of coordinately regulated genes that are expressed in discrete stages of B cell development. Proc. Natl. Acad. Sci., USA 87, 5759–5763.

What is claimed is:

1. A recombinant mouse comprising modified alleles of the recombination activating gene (RAG)-2, the modification being introduced into the mouse genome by homologous recombination in an embryonic stem cell, wherein said modification prevents the expression of functional RAG-2 product and results in a substantial depletion of mature lymphocytes.

2. The mouse of claim 1, wherein the mouse is infected with a foreign organism.

3. The mouse of claim 2, wherein the foreign organism is selected from the group consisting of bacteria, mycoplasma, fungi, protozoa, and parasites.

4. The mouse of claim 3, wherein the foreign organism is selected from the group consisting of *Borrelia burgdorferi* and *Pneumocystis carinii*.

5. The mouse of claim 1, wherein VDJ recombination in lymphocytes of the mouse is inhibited.

6. The mouse of claim 1, further comprising a selectable marker gene inserted in the recombination activating gene-2.

7. The mouse of claim 6, comprising two selectable marker genes inserted in the recombination activating gene-2.

8. The mouse of claim 6, wherein the selectable marker gene is selected from the group consisting of a neomycin resistance gene, a thymidine kinass gene, an adenine phosphoribosyl transferase gene, a hypoxanthine-guanine phosphoribosyl transferase gene, and a dihydrofolate reductase gene.

9. A process of producing the mouse of claim 1 which comprises:

a) modifying a RAG-2 to produce functionally deficient RAG-2 product;
   b) introducing the modified RAG-2 into the genome of the mouse;
   c) identifying mice containing the modified RAG-2; and
   d) generating modified RAG-2 carrying mouse which is RAG-2 functionally deficient.

10. The process of claim 9, wherein the modification of a RAG-2 further comprises:

a) cloning a RAG-2 in a cloning vehicle; and
   b) altering the RAG-2 by either addition, deletion or mutation of at least one nucleotide.

11. The process of claim 10 further comprising insertion of a selectable marker gene.

12. The process recited in claim 11, wherein the selectable marker gene is neomycin resistance gene.

13. The process of claim 12, wherein the modified RAG-2 is introduced to the genome of the mouse by microinjection.

14. The process of claim 9, wherein the introduction of the modified RAG-2 further comprises:

a) introducing the modified RAG-2 to embryonic stem cells;
   c) identifying embryonic cells carrying the modified RAG-2; and
   d) introducing the selected embryonic stem cells which carry the modified RAG-2 to the blastocyte of a developing embryo.

15. The process of claim 14, wherein a RAG-2 is cloned in a cloning vehicle and modified by insertion of at least one selectable marker gene, further comprising:

a) inserting a negatively selectable marker gene next to the modified RAG-2 whereby the distance between the marker gene and the modified RAG-2 is sufficient to carry out homologous recombination;
   b) introducing the modified gene to embryonic stem cells;
   c) positively selecting the marker which modifies the RAG-2 and negatively selects the inserted adjacent marker; and
   d) introducing the selected embryonic stem cells which carry the modified RAG-2 to the blastocyte of a developing embryo.

16. The process of claim 10, wherein where in step b) the plasmid G3E2-12, recited in FIG. 1, with ATCC designation number 75198, is introduced into mouse embryonic stem cells, producing a modified mouse embryonic stem cell line.

17. The process of claim 16, wherein the modified mouse embryonic stem cell line is B47, with ATCC designation number ATCC CRL 10971.

18. A method for evaluating drugs against infection, comprising:

a) infecting the mouse of claim 1 with a known infectious agent;
   b) administering a drug or different combination of drugs to the mouse; and
   c) monitoring the effect of the treatment.

* * * * *